(12) United States Patent
Heinzman et al.

(10) Patent No.: US 10,696,821 B2
(45) Date of Patent: Jun. 30, 2020

(54) FIBROUS ELEMENTS COMPRISING FAST WETTING SURFACTANTS AND METHODS FOR MAKING SAME

(71) Applicant: The Procter & Gamble Company, Cincinnati, OH (US)

(72) Inventors: Stephen Wayne Heinzman, Cincinnati, OH (US); Brooke Marie Woods, Springfield, OH (US); Michael David James, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 307 days.

(21) Appl. No.: 13/865,443

(22) Filed: Apr. 18, 2013

(65) Prior Publication Data
US 2013/0280508 A1 Oct. 24, 2013

Related U.S. Application Data

(60) Provisional application No. 61/635,433, filed on Apr. 19, 2012.

(51) Int. Cl.
*C08L 3/02* (2006.01)
*D01F 6/14* (2006.01)
(Continued)

(52) U.S. Cl.
CPC ................ *C08L 3/02* (2013.01); *A47K 10/00* (2013.01); *B32B 5/022* (2013.01); *B32B 5/08* (2013.01); *B32B 5/12* (2013.01); *B32B 5/26* (2013.01); *D01F 1/10* (2013.01); *D01F 2/00* (2013.01); *D01F 4/00* (2013.01); *D01F 6/14* (2013.01); *D04H 1/4309* (2013.01); *D04H 1/541* (2013.01); *D04H 1/64* (2013.01); *D21H 17/37* (2013.01); *D21H 17/375* (2013.01); *D21H 21/24* (2013.01); *B32B 2262/0223* (2013.01); *B32B 2262/0261* (2013.01);
(Continued)

(58) Field of Classification Search
CPC . B32B 5/022; B32B 2555/02; B32B 2555/00; D04H 1/541; D21H 21/24; D21H 27/002; D21H 27/005; D21H 21/00; D01F 1/10; Y10T 428/27; C08L 3/02
See application file for complete search history.

(56) References Cited

U.S. PATENT DOCUMENTS 6,709,526 B1 3/2004 Bailey et al.
6,814,904 B1 11/2004 Bauer et al.
(Continued)

FOREIGN PATENT DOCUMENTS

EP 1 217 106 A1 6/2002

OTHER PUBLICATIONS

D Aircraft Products, Inc, AEROSOL TR-70 Surfactant, 2020, http://www.industrycortex.com/datasheets/profile/4333753 (Year: 2020).*

(Continued)

*Primary Examiner* — Scott R. Walshon
*Assistant Examiner* — Jasper Saberi
(74) *Attorney, Agent, or Firm* — C. Brant Cook

(57) ABSTRACT

Fibrous elements, such as filaments and/or fibers, and more particularly to fibrous elements that contain a fast wetting surfactant, fibrous structures made therefrom, and methods for making same are provided.

16 Claims, 9 Drawing Sheets

(51) Int. Cl.

| | | |
|---|---|---|
| *D21H 27/00* | (2006.01) | |
| *A47K 10/00* | (2006.01) | |
| *D04H 1/4309* | (2012.01) | |
| *D01F 2/00* | (2006.01) | |
| *D01F 4/00* | (2006.01) | |
| *D21H 21/24* | (2006.01) | |
| *D01F 1/10* | (2006.01) | |
| *D04H 1/541* | (2012.01) | |
| *B32B 5/26* | (2006.01) | |
| *D04H 1/64* | (2012.01) | |
| *D21H 17/37* | (2006.01) | |
| *B32B 5/08* | (2006.01) | |
| *B32B 5/12* | (2006.01) | |
| *B32B 5/02* | (2006.01) | |

(52) U.S. Cl.
CPC ..... *B32B 2307/54* (2013.01); *B32B 2307/542* (2013.01); *B32B 2307/718* (2013.01); *B32B 2307/726* (2013.01); *B32B 2555/00* (2013.01); *B32B 2555/02* (2013.01); *D21H 27/002* (2013.01); *Y10T 442/10* (2015.04)

(56) References Cited

U.S. PATENT DOCUMENTS

| | | |
|---|---|---|
| 7,704,601 B2 | 4/2010 | Manifold et al. |
| 8,815,784 B2 | 8/2014 | Ogle et al. |
| 2002/0188041 A1 | 12/2002 | Bailey et al. |
| 2004/0043685 A1 | 3/2004 | Goldwasser |
| 2004/0163781 A1* | 8/2004 | Hernandez-Munoa et al. ............. 162/91 |
| 2005/0026529 A1 | 2/2005 | Bond et al. |
| 2005/0130539 A1* | 6/2005 | Allen et al. .................. 442/364 |
| 2006/0275347 A1 | 12/2006 | Evers Smith et al. |
| 2008/0000602 A1 | 1/2008 | Dyer et al. |
| 2008/0154225 A1 | 6/2008 | Phan |
| 2009/0025894 A1 | 1/2009 | Barnholtz et al. |
| 2009/0104430 A1* | 4/2009 | Cordial et al. ............. 428/322.7 |
| 2010/0104863 A1 | 4/2010 | Bailey et al. |
| 2011/0039054 A1 | 2/2011 | Cabell et al. |
| 2011/0039074 A1* | 2/2011 | Cabell et al. ................. 428/166 |
| 2011/0039469 A1 | 2/2011 | Cabell et al. |
| 2011/0223422 A1* | 9/2011 | Forshey .................. C08L 29/04 428/401 |
| 2012/0021026 A1 | 1/2012 | Glenn et al. |
| 2013/0280503 A1 | 10/2013 | Cabell et al. |
| 2013/0280979 A1 | 10/2013 | McKee et al. |

OTHER PUBLICATIONS

U.S. Appl. No. 13/865,482, filed Apr. 18, 2013, McKee.
U.S. Appl. No. 13/868,155, filed Apr. 23, 2013, Cabell, et al.
International Search Report dated Jul. 2, 2013.
All Office Actions in U.S. Appl. No. 13/865,443, U.S. Appl. No. 13/865,482, and U.S. Appl. No. 13/868,155.

* cited by examiner

FIBROUS ELEMENTS COMPRISING FAST WETTING SURFACTANTS AND METHODS FOR MAKING SAME

FIELD OF THE INVENTION

The present invention relates to fibrous elements, such as filaments and/or fibers, and more particularly to fibrous elements that comprise a fast wetting surfactant, fibrous structures made therefrom, and methods for making same.

BACKGROUND OF THE INVENTION

Fibrous elements, especially produced from spinning processes such as meltblow and/or spunbond processes are known in the art. However, a vast majority of such spinning processes utilize non-aqueous polymer melt compositions, typically comprising thermoplastic and/or thermoset polymers that utilize the effects of cooling the non-aqueous polymer melt compositions to produce the fibrous elements during the spinning processes.

In cases where the fibrous elements are produced from aqueous polymer melt compositions, for example polymer melt compositions comprising hydroxyl polymers, such as polysaccharides, hot drying air is used to remove water from the aqueous polymer melt compositions during spinning in order to produce the fibrous elements, which may be collected to form a fibrous structure. Removal of water from the incipient fibrous elements aids in inhibiting the fibrous elements from sticking to one another during the spinning and/or collecting processes. Failure to effectively remove water from the fibrous elements during formation results in relatively poor tensile properties, such as relatively lower fail stretch (FS), relatively lower total dry tensile (TDT), and/or relatively lower total energy absorbed (TEA), in the fibrous structures produced from the ineffectively dried fibrous elements. It is believed that these poor tensile properties in the fibrous structure are caused, at least in part, by excessive bonding of fibrous elements to one another that occurs when the fibrous elements are not effectively dried. However, the use of larger amounts of drying air is economically infeasible and energy intensive. In addition, ineffectively dried fibrous elements exhibit relatively larger average diameters, which impact various properties of the fibrous structures produced therefrom.

As shown above, a problem encountered by formulators is how to remove water more effectively from fibrous elements formed from aqueous polymer melt compositions without using increased levels of drying air to form the fibrous elements.

Therefore, there is a need for fibrous elements produced from aqueous polymer melt compositions and fibrous structures made therefrom that avoid the negatives discussed above.

SUMMARY OF THE INVENTION

The present invention fulfills the need described above by providing a fibrous element comprising a fast wetting surfactant, a fibrous structure formed therefrom, and a method for making such a fibrous element and/or fibrous structure.

A solution to the problem identified above is to incorporate a fast wetting surfactant into the aqueous polymer melt composition such that the water from the fibrous elements formed from the aqueous polymer melt composition is more effectively removed without increasing the level of drying air used to form the fibrous elements.

In one example of the present invention, a fibrous element comprising a blend comprising a fibrous element-forming polymer, such as a hydroxyl polymer, and a fast wetting surfactant, is provided.

In another example of the present invention, a fibrous structure comprising a plurality of fibrous elements of the present invention, is provided.

In still another example of the present invention, an aqueous polymer melt composition comprising a fibrous element-forming polymer, such as a hydroxyl polymer, and a fast wetting surfactant, is provided.

In yet another example of the present invention, a polymeric structure, such as a fibrous element, derived from an aqueous polymer melt composition of the present invention, is provided.

In still yet another example of the present invention, a method for making a fibrous element of the present invention comprising the steps of:
 a. providing an aqueous polymer melt composition comprising a fibrous element-forming polymer, such as a hydroxyl polymer, and a fast wetting surfactant; and
 b. polymer processing the aqueous polymer melt composition such that one or more fibrous elements are formed, is provided.

In even still yet another example of the present invention, a method for making a polymeric structure of the present invention comprising the steps of:
 a. providing an aqueous polymer melt composition comprising a fibrous element-forming polymer, such as a hydroxyl polymer, and a fast wetting surfactant; and
 b. polymer processing the aqueous polymer melt composition such that one or more polymeric structures are formed, is provided.

In even yet another example of the present invention, a method for making a fibrous structure of the present invention comprising the steps of:
 a. providing an aqueous polymer melt composition comprising a fibrous element-forming polymer, such as a hydroxyl polymer, and a fast wetting surfactant; and
 b. polymer processing the aqueous polymer melt composition such that a plurality of fibrous elements are formed;
 c. collecting the fibrous elements on a collection device such that a fibrous structure is formed, is provided.

In even still another example of the present invention, a single- or multi-ply sanitary tissue product comprising a fibrous structure of the present invention, is provided.

Accordingly, the present invention relates to polymeric structures, such as fibrous elements, comprising fast wetting surfactants, fibrous structures made from such fibrous elements, and processes for making same.

DETAILED DESCRIPTION OF THE INVENTION

Definitions

Figure 1:
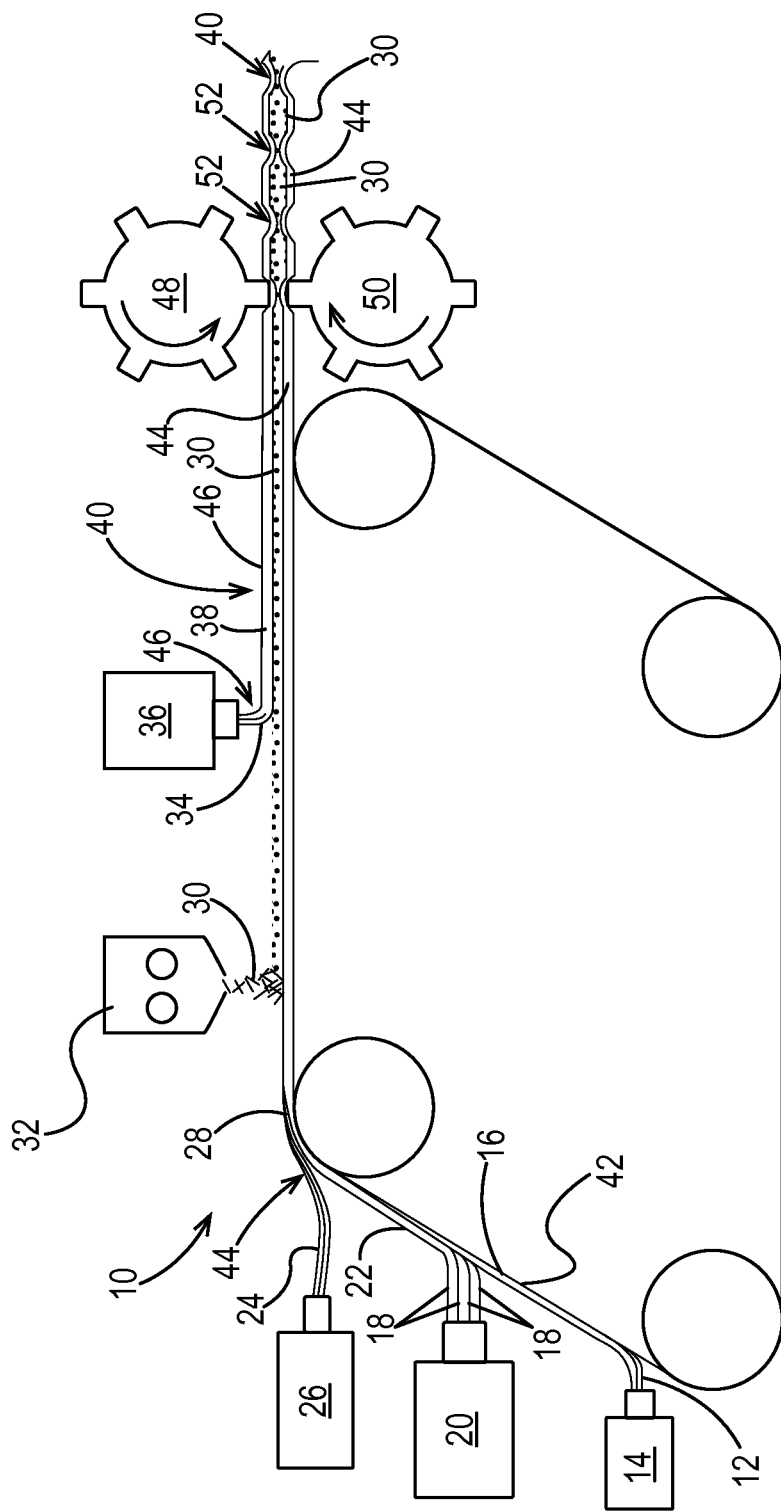
FIG. 1 is a schematic representation of one example of a method for making a fibrous structure according to the present invention.

"Fibrous structure" as used herein means a structure that comprises one or more fibrous elements. In one example, a fibrous structure according to the present invention means an association of fibrous elements that together form a structure capable of performing a function.

Non-limiting examples of processes for making fibrous structures include known wet-laid papermaking processes, air-laid papermaking processes, and wet, solution, and dry filament spinning processes, for example meltblowing and spunbonding spinning processes that are typically referred to as nonwoven processes. Further processing of the formed fibrous structure may be carried out such that a finished fibrous structure is formed. For example, in typical papermaking processes, the finished fibrous structure is the fibrous structure that is wound on the reel at the end of papermaking. The finished fibrous structure may subsequently be converted into a finished product, e.g. a sanitary tissue product.

"Fibrous element" as used herein means an elongate particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from polymer melt compositions via suitable spinning operations, such as meltblowing and/or spunbonding and/or they may be obtained from natural sources such as vegetative sources, for example trees.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol, thermoplastic polymer, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include pulp fibers, such as wood pulp fibers, and synthetic staple fibers such as polypropylene, polyethylene, polyester, copolymers thereof, rayon, glass fibers and polyvinyl alcohol fibers.

Staple fibers may be produced by spinning a filament tow and then cutting the tow into segments of less than 5.08 cm (2 in.) thus producing fibers.

In one example of the present invention, a fiber may be a naturally occurring fiber, which means it is obtained from a naturally occurring source, such as a vegetative source, for example a tree and/or plant. Such fibers are typically used in papermaking and are oftentimes referred to as papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to fibrous structures made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. Also applicable to the present invention are fibers derived from recycled paper, which may contain any or all of the above categories of fibers as well as other non-fibrous polymers such as fillers, softening agents, wet and dry strength agents, and adhesives used to facilitate the original papermaking.

In addition to the various wood pulp fibers, other cellulosic fibers such as cotton linters, rayon, lyocell, and bagasse fibers can be used in the fibrous structures of the present invention.

"Sanitary tissue product" as used herein means a soft, relatively low density fibrous structure useful as a wiping implement for post-urinary and post-bowel movement cleaning (toilet tissue), for otorhinolaryngological discharges (facial tissue), multi-functional absorbent and cleaning uses (absorbent towels) and wipes, such as wet and dry wipes. The sanitary tissue product may be convolutedly wound upon itself about a core or without a core to form a sanitary tissue product roll or may be in the form of discrete sheets.

In one example, the sanitary tissue product of the present invention comprises one or more fibrous structures according to the present invention. The fibrous structure and/or sanitary tissue products may be embossed.

The sanitary tissue products and/or fibrous structures of the present invention may exhibit a basis weight between about 10 g/m² to about 120 g/m² and/or from about 15 g/m² to about 110 g/m² and/or from about 20 g/m² to about 100 g/m² and/or from about 30 to 90 g/m² as determined by the Basis Weight Test Method described herein. In addition, the sanitary tissue product of the present invention may exhibit a basis weight between about 40 g/m² to about 120 g/m² and/or from about 50 g/m² to about 110 g/m² and/or from about 55 g/m² to about 105 g/m² and/or from about 60 g/m² to 100 g/m² as determined by the Basis Weight Test Method described herein.

The sanitary tissue products of the present invention may exhibit a total dry tensile of greater than about 59 g/cm (150 g/in) and/or from about 78 g/cm (200 g/in) to about 394 g/cm (1000 g/in) and/or from about 98 g/cm (250 g/in) to about 335 g/cm (850 g/in) as measured according to the Dry Tensile Test Method described herein. In addition, the sanitary tissue product of the present invention may exhibit a total dry tensile of greater than about 196 g/cm (500 g/in) and/or from about 196 g/cm (500 g/in) to about 394 g/cm (1000 g/in) and/or from about 216 g/cm (550 g/in) to about 335 g/cm (850 g/in) and/or from about 236 g/cm (600 g/in) to about 315 g/cm (800 g/in). In one example, the sanitary tissue product exhibits a total dry tensile of less than about 394 g/cm (1000 g/in) and/or less than about 335 g/cm (850 g/in).

The sanitary tissue products of the present invention may exhibit an initial total wet tensile of less than about 78 g/cm (200 g/in) and/or less than about 59 g/cm (150 g/in) and/or less than about 39 g/cm (100 g/in) and/or less than about 29 g/cm (75 g/in) and/or less than about 23 g/cm (60 g/in) as measured according to the Initial Total Wet Tensile Test Method described herein.

The sanitary tissue products of the present invention may exhibit an initial total wet tensile of greater than about 118 g/cm (300 g/in) and/or greater than about 157 g/cm (400 g/in) and/or greater than about 196 g/cm (500 g/in) and/or greater than about 236 g/cm (600 g/in) and/or greater than about 276 g/cm (700 g/in) and/or greater than about 315 g/cm (800 g/in) and/or greater than about 354 g/cm (900 g/in) and/or greater than about 394 g/cm (1000 g/in) and/or from about 118 g/cm (300 g/in) to about 1968 g/cm (5000 g/in) and/or from about 157 g/cm (400 g/in) to about 1181 g/cm (3000 g/in) and/or from about 196 g/cm (500 g/in) to about 984 g/cm (2500 g/in) and/or from about 196 g/cm (500 g/in) to about 787 g/cm (2000 g/in) and/or from about 196 g/cm (500 g/in) to about 591 g/cm (1500 g/in).

The sanitary tissue products of the present invention may exhibit a density of less than 0.60 g/cm³ and/or less than 0.30 g/cm³ and/or less than 0.20 g/cm³ and/or less than 0.15 g/cm³ and/or less than 0.10 g/cm³ and/or less than 0.07 g/cm³ and/or less than 0.05 g/cm³ and/or from about 0.01 g/cm³ to about 0.20 g/cm³ and/or from about 0.02 g/cm³ to about 0.15 g/cm³ and/or from about 0.02 g/cm³ to about 0.10 g/cm³.

The sanitary tissue products of the present invention may be in the form of sanitary tissue product rolls. Such sanitary tissue product rolls may comprise a plurality of connected, but perforated sheets of fibrous structure, that are separably dispensable from adjacent sheets.

The sanitary tissue products of the present invention may comprise additives such as softening agents, temporary wet strength agents, permanent wet strength agents, bulk softening agents, lotions, silicones, wetting agents, latexes, patterned latexes and other types of additives suitable for inclusion in and/or on sanitary tissue products.

"Scrim" as used herein means a material that is used to overlay solid additives within the fibrous structures of the present invention such that the solid additives are positioned between the scrim and a layer of the fibrous structure. In one example, the scrim covers the solid additives such that they are positioned between the scrim and the nonwoven substrate of the fibrous structure. In another example, the scrim is a minor component relative to the nonwoven substrate of the fibrous structure.

"Hydroxyl polymer" as used herein includes any hydroxyl-containing polymer that can be incorporated into a fibrous structure of the present invention, such as into a fibrous structure in the form of a fibrous element. In one example, the hydroxyl polymer of the present invention includes greater than 10% and/or greater than 20% and/or greater than 25% by weight hydroxyl moieties. In another example, the hydroxyl within the hydroxyl-containing polymer is not part of a larger functional group such as a carboxylic acid group.

"Non-thermoplastic" as used herein means, with respect to a material, such as a fibrous element as a whole and/or a polymer within a fibrous element, that the fibrous element and/or polymer exhibits no melting point and/or softening point, which allows it to flow under pressure, in the absence of a plasticizer, such as water, glycerin, sorbitol, urea and the like.

"Thermoplastic" as used herein means, with respect to a material, such as a fibrous element as a whole and/or a polymer within a fibrous element, that the fibrous element and/or polymer exhibits a melting point and/or softening point at a certain temperature, which allows it to flow under pressure.

"Non-cellulose-containing" as used herein means that less than 5% and/or less than 3% and/or less than 1% and/or less than 0.1% and/or 0% by weight of cellulose polymer, cellulose derivative polymer and/or cellulose copolymer is present in fibrous element. In one example, "non-cellulose-containing" means that less than 5% and/or less than 3% and/or less than 1% and/or less than 0.1% and/or 0% by weight of cellulose polymer is present in fibrous element.

"Fast wetting surfactant" as used herein means a surfactant that exhibits a Critical Micelle Concentration of greater 0.15% by weight and/or at least 0.25% and/or at least 0.50% and/or at least 0.75% and/or at least 1.0% and/or at least 1.25% and/or at least 1.4% and/or less than 10.0% and/or less than 7.0% and/or less than 4.0% and/or less than 3.0% and/or less than 2.0% by weight.

"Aqueous polymer melt composition" as used herein means a composition comprising water and a melt processed polymer, such as a melt processed fibrous element-forming polymer, for example a melt processed hydroxyl polymer.

"Melt processed fibrous element-forming polymer" as used herein means any polymer, which by influence of elevated temperatures, pressure and/or external plasticizers may be softened to such a degree that it can be brought into a flowable state, and in this condition may be shaped as desired.

"Melt processed hydroxyl polymer" as used herein means any polymer that contains greater than 10% and/or greater than 20% and/or greater than 25% by weight hydroxyl groups and that has been melt processed, with or without the aid of an external plasticizer. More generally, melt processed hydroxyl polymers include polymers, which by the influence of elevated temperatures, pressure and/or external plasticizers may be softened to such a degree that they can be brought into a flowable state, and in this condition may be shaped as desired.

"Blend" as used herein means that two or more materials, such as a fibrous element-forming polymer, for example a hydroxyl polymer, and a fast wetting surfactant are in contact with each other, such as mixed together homogeneously or non-homogeneously, within a polymeric structure, such as a fibrous element. In other words, a polymeric structure, such as a fibrous element, formed from one material, but having an exterior coating of another material is not a blend of materials for purposes of the present invention. However, a fibrous element formed from two different materials is a blend of materials for purposes of the present invention even if the fibrous element further comprises an exterior coating of a material.

"Associate," "Associated," "Association," and/or "Associating" as used herein with respect to fibrous elements means combining, either in direct contact or in indirect contact, fibrous elements such that a fibrous structure is formed. In one example, the associated fibrous elements may be bonded together for example by adhesives and/or thermal bonds. In another example, the fibrous elements may be associated with one another by being deposited onto the same fibrous structure making belt.

"Weight average molecular weight" as used herein means the weight average molecular weight as determined using gel permeation chromatography as generally described in Colloids and Surfaces A. Physico Chemical & Engineering Aspects, Vol. 162, 2000, pg. 107-121 and detailed in the Weight Average Molecular Weight Test Method described herein.

"Average Diameter" as used herein, with respect to a fibrous element, is measured according to the Average Diameter Test Method described herein. In one example, a fibrous element of the present invention exhibits an average diameter of less than 50 µm and/or less than 25 µm and/or less than 20 µm and/or less than 15 µm and/or less than 10 µm and/or less than 6 µm and/or greater than 1 µm and/or greater than 3 µm as measured according to the Average Diameter Test Method described herein.

"Basis Weight" as used herein is the weight per unit area of a sample reported in lbs/3000 ft$^2$ or g/m$^2$ as determined by the Basis Weight Test Method described herein.

"Machine Direction" or "MD" as used herein means the direction parallel to the flow of the fibrous structure through a fibrous structure making machine and/or sanitary tissue product manufacturing equipment. Typically, the MD is substantially perpendicular to any perforations present in the fibrous structure "Cross Machine Direction" or "CD" as used herein means the direction perpendicular to the machine direction in the same plane of the fibrous structure and/or sanitary tissue product comprising the fibrous structure.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Fibrous Elements

The fibrous elements of the present invention comprise a fibrous element-forming polymer, such as a hydroxyl polymer and a fast wetting surfactant. In one example, the fibrous elements may comprise two or more fibrous element-forming polymers, such as two or more hydroxyl polymers. In another example, the fibrous elements may comprise two or more fast wetting surfactants. In another example, the fibrous elements may comprise two or more surfactants at least one of which is a fast wetting surfactant, such as Aerosol® MA-80, and one of which is not a fast wetting surfactant, such as Aerosol® OT. In another example, the fibrous element may comprise two or more fibrous element-forming polymers, such as two or more hydroxyl polymers, at least one of which is starch and/or a starch derivative and one of which is a non-starch and/or non-starch derivative, such as polyvinyl alcohol. In one example, the fibrous element comprises a filament. In another example, the fibrous element comprises a fiber.

Fibrous Element-Forming Polymers

The aqueous polymer melt compositions of the present invention and/or fibrous elements, such as filaments and/or fibers, of the present invention that associate to form the fibrous structures of the present invention contain at least one fibrous element-forming polymer, such as a hydroxyl polymer, and may contain other types of polymers such as non-hydroxyl polymers that exhibit weight average molecular weights of greater than 500,000 g/mol, and mixtures thereof as determined by the Weight Average Molecular Weight Test Method described herein.

Non-limiting examples of hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose, cellulose derivatives such as cellulose ether and ester derivatives, cellulose copolymers, hemicellulose, hemicellulose derivatives, hemicellulose copolymers, gums, arabinans, galactans, proteins and various other polysaccharides and mixtures thereof.

In one example, a hydroxyl polymer of the present invention comprises a polysaccharide.

In another example, a hydroxyl polymer of the present invention comprises a non-thermoplastic polymer.

The hydroxyl polymer may have a weight average molecular weight of from about 10,000 g/mol to about 40,000,000 g/mol and/or greater than 100,000 g/mol and/or greater than 1,000,000 g/mol and/or greater than 3,000,000 g/mol and/or greater than 3,000,000 g/mol to about 40,000,000 g/mol as determined by the Weight Average Molecular Weight Test Method described herein. Higher and lower molecular weight hydroxyl polymers may be used in combination with hydroxyl polymers having a certain desired weight average molecular weight.

Well known modifications of hydroxyl polymers, such as natural starches, include chemical modifications and/or enzymatic modifications. For example, natural starch can be acid-thinned, hydroxy-ethylated, hydroxy-propylated, and/or oxidized. In addition, the hydroxyl polymer may comprise dent corn starch.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, vinylidene chloride, vinyl chloride, vinyl amine and a variety of acrylate esters. Polyvinyl alcohols comprise the various hydrolysis products formed from polyvinyl acetate. In one example the level of hydrolysis of the polyvinyl alcohols is greater than 70% and/or greater than 88% and/or greater than 95% and/or about 99%.

"Polysaccharides" as used herein means natural polysaccharides and polysaccharide derivatives and/or modified polysaccharides. Suitable polysaccharides include, but are not limited to, starches, starch derivatives, starch copolymers, chitosan, chitosan derivatives, chitosan copolymers, cellulose, cellulose derivatives, cellulose copolymers, hemicellulose, hemicellulose derivatives, hemicelluloses copolymers, gums, arabinans, galactans, and mixtures thereof. The polysaccharide may exhibit a weight average molecular weight of from about 10,000 to about 40,000,000 g/mol and/or greater than about 100,000 and/or greater than about 1,000,000 and/or greater than about 3,000,000 and/or greater than about 3,000,000 to about 40,000,000 as determined by the Weight Average Molecular Weight Test Method described herein.

The polysaccharides of the present invention may comprise non-cellulose and/or non-cellulose derivative and/or non-cellulose copolymer hydroxyl polymers. Non-limiting example of such non-cellulose polysaccharides may be selected from the group consisting of: starches, starch derivatives, starch copolymers, chitosan, chitosan derivatives, chitosan copolymers, hemicellulose, hemicellulose derivatives, hemicelluloses copolymers, and mixtures thereof.

In one example, the hydroxyl polymer comprises starch, a starch derivative and/or a starch copolymer. In another example, the hydroxyl polymer comprises starch and/or a starch derivative. In yet another example, the hydroxyl polymer comprises starch. In one example, the hydroxyl polymer comprises ethoxylated starch. In another example, the hydroxyl polymer comprises acid-thinned starch.

As is known, a natural starch can be modified chemically or enzymatically, as well known in the art. For example, the natural starch can be acid-thinned, hydroxy-ethylated, hydroxy-propylated, ethersuccinylated or oxidized. In one example, the starch comprises a high amylopectin natural starch (a starch that contains greater than 75% and/or greater than 90% and/or greater than 98% and/or about 99% amylopectin). Such high amylopectin natural starches may be derived from agricultural sources, which offer the advantages of being abundant in supply, easily replenishable and relatively inexpensive. Chemical modifications of starch typically include acid or alkaline-catalyzed hydrolysis and chain scission (oxidative and/or enzymatic) to reduce molecular weight and molecular weight distribution. Suitable compounds for chemical modification of starch include organic acids such as citric acid, acetic acid, glycolic acid, and adipic acid; inorganic acids such as hydrochloric acid, sulfuric acid, nitric acid, phosphoric acid, boric acid, and partial salts of polybasic acids, e.g., $KH_2PO_4$, $NaHSO_4$; group Ia or IIa metal hydroxides such as sodium hydroxide, and potassium hydroxide; ammonia; oxidizing agents such as hydrogen peroxide, benzoyl peroxide, ammonium persulfate, potassium permanganate, hypochloric salts, and the like; and mixtures thereof.

"Modified starch" is a starch that has been modified chemically or enzymatically. The modified starch is contrasted with a native starch, which is a starch that has not been modified, chemically or otherwise, in any way.

Chemical modifications may also include derivatization of starch by reaction of its hydroxyl groups with alkylene oxides, and other ether-, ester-, urethane-, carbamate-, or isocyanate-forming substances. Hydroxyalkyl, ethersuccinylated, acetyl, or carbamate starches or mixtures thereof can be used as chemically modified starches. The degree of substitution of the chemically modified starch is from 0.001 to 3.0, and more specifically from 0.003 to 0.2. Biological modifications of starch may include bacterial digestion of the carbohydrate bonds, or enzymatic hydrolysis using enzymes such as amylase, amylopectase, and the like.

Generally, all kinds of natural starches can be used in the present invention. Suitable naturally occurring starches can include, but are not limited to: corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches, particularly corn starch and wheat starch, can be particularly beneficial due to their low cost and availability.

In order to generate the required rheological properties for high-speed spinning processes, the molecular weight of the natural, unmodified starch should be reduced. The optimum molecular weight is dependent on the type of starch used. For example, a starch with a low level of amylose component, such as a waxy maize starch, disperses rather easily in an aqueous solution with the application of heat and does not retrograde or recrystallize significantly. With these properties, a waxy maize starch can be used at a weight average molecular weight, for example in the range of 500,000 g/mol to 40,000,000 g/mol as determined by the Weight Average Molecular Weight Test Method described herein. Modified starches such as hydroxy-ethylated Dent corn starch, which contains about 25% amylose, or oxidized Dent corn starch tend to retrograde more than waxy maize starch but less than acid thinned starch. This retrogradation, or recrystallization, acts as a physical cross-linking to effectively raise the weight average molecular weight of the starch in aqueous solution. Therefore, an appropriate weight average molecular weight for a typical commercially available hydroxyethylated Dent corn starch with 2 wt. % hydroxyethylation or oxidized Dent corn starch is from about 200,000 g/mol to about 10,000,000 g/mol. For ethoxylated starches with higher degrees of ethoxylation, for example a hydroxyethylated Dent corn starch with 5 wt % hydroxyethylation, weight average molecular weights of up to 40,000,000 g/mol as determined by the Weight Average Molecular Weight Test Method described herein may be suitable for the present invention. For acid thinned Dent corn starch, which tends to retrograde more than oxidized Dent corn starch, the appropriate weight average molecular weight is from about 100,000 g/mol to about 15,000,000 g/mol as determined by the Weight Average Molecular Weight Test Method described herein.

The weight average molecular weight of starch may also be reduced to a desirable range for the present invention by physical/mechanical degradation (e.g., via the thermomechanical energy input of the processing equipment).

The natural starch can be hydrolyzed in the presence of an acid catalyst to reduce the molecular weight and molecular weight distribution of the composition. The acid catalyst can be selected from the group consisting of hydrochloric acid, sulfuric acid, phosphoric acid, citric acid, ammonium chloride and any combination thereof. Also, a chain scission agent may be incorporated into a spinnable starch composition such that the chain scission reaction takes place substantially concurrently with the blending of the starch with other components. Non-limiting examples of oxidative chain scission agents suitable for use herein include ammonium persulfate, hydrogen peroxide, hypochlorite salts, potassium permanganate, and mixtures thereof. Typically, the chain scission agent is added in an amount effective to reduce the weight average molecular weight of the starch to the desirable range. It is found that compositions having modified starches in the suitable weight average molecular weight ranges have suitable shear viscosities, and thus improve processability of the composition. The improved processability is evident in less interruptions of the process (e.g., reduced breakage, shots, defects, hang-ups) and better surface appearance and strength properties of the final product, such as fibers of the present invention.

In one example, the fibrous element of the present invention is void of thermoplastic, water-insoluble polymers.

Other Polymers

The aqueous polymer melt compositions of the present invention and/or fibrous elements of the present invention may comprise, in addition to the fibrous element-forming polymer, other polymers, such as non-hydroxyl polymers.

Non-limiting examples of suitable non-hydroxyl polymers that may be included in the fibrous elements of the present invention include non-hydroxyl polymers that exhibit a weight average molecular weight of greater than 500,000 g/mol and/or greater than 750,000 g/mol and/or greater than 1,000,000 g/mol and/or greater than 1,250,000 g/mol and/or at greater than 1,400,000 g/mol and/or at least 1,450,000 g/mol and/or at least 1,500,000 g/mol and/or less than 10,000,000 g/mol and/or less than 5,000,000 g/mol and/or less than 2,500.00 g/mol and/or less than 2,000,000 g/mol and/or less than 1,750,000 g/mol as determined by the Weight Average Molecular Weight Test Method described herein.

In one example, the non-hydroxyl polymer exhibits a polydispersity of greater than 1.10 and/or at least 1.20 and/or at least 1.30 and/or at least 1.32 and/or at least 1.40 and/or at least 1.45.

In another example, the non-hydroxyl polymer exhibits a concentration greater than its entanglement concentration (Ce) and/or a concentration greater than 1.2 times its entanglement concentration (Ce) and/or a concentration greater than 1.5 times its entanglement concentration (Ce) and/or a concentration greater than twice its entanglement concentration (Ce) and/or a concentration greater than 3 times its entanglement concentration (Ce).

In yet another example, the non-hydroxyl polymer comprises a linear polymer. In another example, the non-hydroxyl polymer comprises a long chain branched polymer. In still another example, the non-hydroxyl polymer is compatible with the hydroxyl polymer at a concentration greater than the non-hydroxyl polymer's entanglement concentration $C_e$.

Non-limiting examples of suitable non-hydroxyl polymers are selected from the group consisting of: polyacrylamide and its derivatives; polyacrylic acid, polymethacrylic acid and their esters; polyethyleneimine; copolymers made from mixtures of the aforementioned polymers; and mixtures thereof. In one example, the non-hydroxyl polymer comprises polyacrylamide. In one example, the fibrous elements comprises two or more non-hydroxyl polymers, such as two or more polyacrylamides, such at two or more different weight average molecular weight polyacrylamides.

Non-hydroxyl polymers which are substantially compatible with starch are also useful herein as an extensional viscosity spinning aid. "Substantially compatible" means that the non-hydroxyl polymer does not exist as a separate polymer phase from the fibrous element-forming polymer, such as the hydroxyl polymer. The molecular weight of a suitable polymer should be sufficiently high to effectuate entanglements thus increasing the melt strength of the aqueous polymer melt composition in which it is present, and preventing melt fracture during spinning of the aqueous polymer melt composition to produce fibrous elements.

In one example, the non-hydroxyl polymer is at a sufficient concentration and molecular weight such that the polymer chains of the non-hydroxyl polymer are overlapped and form entanglement couplings. For example, the non-hydroxyl polymer concentration is above the entanglement concentration ($c_e$), where $c_e$ is either measured or calculated. For neutral polymers, such as polyacrylamide, in a good solvent, such as water (or other solvent where Rg~$N^{0.6}$ where Rg is the polymer's radius of gyration and N is the polymer molecular weight) or polyelectrolytes in the high salt limit, the following scaling relationships set forth below in Equation (Eq.) (1) below apply.

$$\eta_0 \sim c^{1.25} c < c_e$$

$$\eta_0 \sim c^{4.6} c > c_e \qquad (1)$$

Thus, $c_e$ is experimentally measured by finding the inflection point in the dependence of zero shear viscosity ($\eta_0$) on concentration. The entanglement concentration is also calculated from Eq. (2) below, $$c_e = \frac{M_c}{M_w} \qquad (2)$$

where $M_c$ is the critical entanglement molecular weight of the polymer species, and $M_w$ is the weight average molecular weight. For example, a polyacrylamide (PAAm) with an $M_w$ of 10,000,000 g/mol must be present at ~0.1% ($M_e$ of PAAm is 9100 g/mol) for sufficient entanglement between chains. For $c \ll c_e$, lack of entanglement couplings result in inadequate melt strength, while for $c \gg c_e$ the filament will resist attenuation due to the high degree of strain hardening and melt elasticity. From Eq. (2) a higher or lower molecular weight polymer may be utilized if its concentration is adjusted accordingly such that the PAAm level is above $c_e$.

In one example, the non-hydroxyl polymer comprises a substantially linear chain structure, though a non-hydroxyl polymer having a linear chain having short branches (1-5 monomer units) may also be suitable for use herein. Typically the weight average molecular weight of the non-hydroxyl polymer ranges from about 500,000 g/mol to 10,000,000 g/mol and/or from about 700,000 g/mol to about 5,000,000 g/mol and/or from about 1,000,000 g/mol to about 5,000,000 g/mol as determined by the Weight Average Molecular Weight Test Method described herein. In the melt processing of the aqueous polymer melt composition of the present invention prior to forming the fibrous elements, the weight average molecular weight of the non-hydroxyl polymer may be degraded by shear to about 1,000,000 g/mol to 3,000,000 g/mol as determined by analysis of the fibrous structure with the Degradation of Fibrous Structure Test Method, described herein followed by the Weight Average Molecular Weight Method described herein. Typically, the non-hydroxyl polymers are present in an amount of from about 0.01% to about 10% and/or from about 0.05% to about 5% and/or from about 0.075% to about 2.5% and/or from about 0.1% to about 1%, by weight of the aqueous polymer melt composition, polymeric structure, fibrous element and/or fibrous structure.

Since non-hydroxyl polymers are shear sensitive it is important that $M_w$ from Eq. (2) is the chain length after the non-hydroxyl polymer has been degraded through the melt processing and is in the final fibrous element composition. The average chain length of the non-hydroxyl polymer after melt processing is determined by a combination of the Degradation of Fibrous Structure Test Method followed by the Weight Average Molecular Weight Method both methods described herein.

Non-limiting examples of suitable non-hydroxyl polymers include polyacrylamide and derivatives such as carboxyl modified polyacrylamide polymers and copolymers including polyacrylic, poly(hydroxyethyl acrylic), polymethacrylic acid and their partial esters; vinyl polymers including polyvinylalcohol, polyvinylpyrrolidone, and the like; polyamides; polyalkylene oxides such as polyethylene oxide and mixtures thereof. Copolymers or graft copolymers made from mixtures of monomers selected from the aforementioned polymers are also suitable herein. Non-limiting examples of commercially available polyacrylamides include nonionic polyacrylamides such as N300 from Kemira or Hyperfloc® NF221, NF301, and NF241 from Hychem, Inc.

Fast Wetting Surfactants

Any suitable fast wetting surfactant may be used in the present invention. Non-limiting examples of suitable fast wetting surfactants include surfactants that exhibit a twin-tailed general structure, for example a surfactant that exhibits a structure IA or IB as follows.

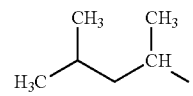

Structure IA

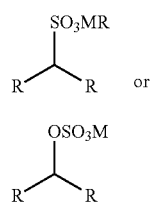

Structure IB wherein R is independently selected from substituted or unsubstituted, linear or branched aliphatic groups and mixtures thereof. In one example, R is independently selected from substituted or unsubstituted, linear or branched $C_4$-$C_7$ aliphatic chains and mixtures thereof. In another example, R is independently selected from substituted or unsubstituted, linear or branched $C_4$-$C_7$ alkyls and mixtures thereof. In another example, R is independently selected from substituted or unsubstituted, linear or branched $C_5$-$C_6$ alkyls and mixtures thereof. In still another example, R is independently selected from substituted or unsubstituted, linear or branched $C_6$ alkyls and mixtures thereof. In even another example, R is an unsubstituted, branched $C_6$ alkyl having the following structure II.

Structure II

In another example, R is independently selected from substituted or unsubstituted, linear or branched $C_5$ alkyls and mixtures thereof. In yet another example, R is independently selected from unsubstituted, linear $C_5$ alkyls and mixtures thereof. The $C_5$ alkyl may comprise a mixture of unsubstituted linear $C_5$ alkyls, for example $C_5$ n-pentyl, and/or 1-methyl branched $C_5$ alkyls as shown in the following structure III.

Structure III

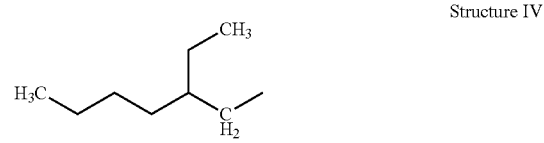

In even another example, R comprises a mixture of $C_4$-$C_7$ alkyls and/or a mixture of $C_5$-$C_6$ alkyls.

The fast wetting surfactants may be present in the polymer melt compositions, fibrous elements, and/or fibrous structures of the present invention, alone or in combination with other non-fast wetting surfactants.

In one example, the fast wetting surfactants of the present invention may be used individually or in mixtures with each other or in a mixture with one or more non-fast wetting surfactants, for example a $C_8$ sulfosuccinate surfactant where R is the following structure IV.

Structure IV

In one example a fast wetting surfactant comprises a sulfosuccinate surfactant having the following structure V.

Structure V wherein R is independently selected from substituted or unsubstituted, linear or branched aliphatic groups and mixtures thereof. In one example, R is independently selected from substituted or unsubstituted, linear or branched $C_4$-$C_7$ aliphatic chains and mixtures thereof. In another example, R is independently selected from substituted or unsubstituted, linear or branched $C_4$-$C_7$ alkyls and mixtures thereof. In another example, R is independently selected from substituted or unsubstituted, linear or branched $C_5$-$C_6$ alkyls and mixtures thereof. In still another example, R is independently selected from substituted or unsubstituted, linear or branched $C_6$ alkyls and mixtures thereof. In even another example, R is an unsubstituted, branched $C_6$ alkyl having the following structure II.

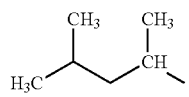

Structure II

Non-limiting examples of fast wetting surfactants according to the present invention include sulfosuccinate surfactants, for example a sulfosuccinate surfactant that has structure II as its R groups (Aerosol® MA-80), a sulfosuccinate surfactant that has $C_4$ isobutyl as its R groups (Aerosol® IB), and a sulfosuccinate surfactant that has a mixture of $C_5$ n-pentyl and structure III as its R groups (Aerosol® AY), all commercially available from Cytec.

Additional non-limiting examples of fast wetting surfactants according to the present invention include alcohol sulfates derived from branched alcohols such as Isalchem and Lial alcohols (from Sasol) ie. Dacpon 27 23 AS and Guerbet alcohols from Lucky Chemical. Still another example of a fast wetting surfactant includes paraffin sulfonates such as Hostapur SAS30 from Clariant.

Typically, the fast wetting surfactants are present in an amount of from about 0.01% to about 5% and/or from about 0.5% to about 2.5% and/or from about 1% to about 2% and/or from about 1% to about 1.5%, by weight of the aqueous polymer melt composition, polymeric structure, fibrous element and/or fibrous structure.

In one example, the fast wetting surfactants of the present invention exhibit a Minimum Surface Tension in Distilled Water of less than 34.0 and/or less than 33.0 and/or less than 32.0 and/or less than 31.0 and/or less than 30.0 and/or less than 29.0 and/or less than 28.0 and/or less than 27.0 and/or less than 26.75 and/or less than 26.5 and/or less than 26.2 and/or less than 25.0 mN/m and/or to greater than 0 and/or greater than 1.0 mN/m.

In still another example, the fast wetting surfactants of the present invention exhibit a CMC of greater than 0.15% and/or at least 0.25% and/or at least 0.50% and/or at least 0.75% and/or at least 1.0% and/or at least 1.25% and/or at least 1.4% and/or less than 10.0% and/or less than 7.0% and/or less than 4.0% and/or less than 3.0% and/or less than 2.0% by weight and a Minimum Surface Tension in Distilled Water of less than 34.0 and/or less than 33.0 and/or less than 32.0 and/or less than 31.0 and/or less than 30.0 and/or less than 29.0 and/or less than 28.0 and/or less than 27.0 and/or less than 26.75 and/or less than 26.5 and/or less than 26.2 and/or less than 25.0 mN/m and/or to greater than 0 and/or greater than 1.0 mN/m. In even another example, the fast wetting surfactants of the present invention exhibit a CMC of at least 1.0% and/or at least 1.25% and/or at least 1.4% and/or less than 4.0% and/or less than 3.0% and/or less than 2.0% by weight and a Minimum Surface Tension in Distilled Water of less than 34.0 and/or less than 33.0 and/or less than 32.0 and/or less than 31.0 and/or less than 30.0 and/or less than 29.0 and/or less than 28.0 and/or less than 27.0 and/or less than 26.75 and/or less than 26.5 and/or less than 26.2 and/or less than 25.0 mN/m and/or to greater than 0 and/or greater than 1.0 mN/m. CMC and Minimum Surface Tension in Distilled Water values of surfactants can be measured by any suitable methods known in the art, for example those methods described in Principles of Colloid and Surface Chemistry, p370-375, incorporated herein by reference.

Table 1 below shows properties of a non-fast wetting surfactant, three fast wetting surfactants, and one mixture of a fast wetting surfactant and a non-fast wetting surfactant, alone and in fibrous elements that form a fibrous structure and compared to a fibrous structure comprising fibrous elements that are void of surfactants. As mentioned above, the CMC and Minimum Surface Tension in Distilled Water are measured by any suitable method known in the art, for example the methods described in Paul C. Hiemenz and Raj Rajagopalan, Principles of Colloid and Surface Chemistry $3^{rd}$ Edition, p253-255, incorporated herein by reference. The wetting rate of a fibrous structure is determined by the Wetting Rate Test Method described herein with from 0.5% to 1.5% by weight total surfactant in the fibrous structure.

TABLE 1

| Surfactant | R Aliphatic Group | CMC wt % | Minimum Surface Tension in Distilled Water (mN/m) | Wetting Rate |
|---|---|---|---|---|
| No Surfactant | NA | NA | NA | −78 |
| Aerosol ® OT (AOT) Non-Fast Wetting Surfactant | $C_8$ (IV) | 0.10-0.15 | 26.2 | −185 |
| Fast Wetting Surfactant 1 (Aerosol ® MA-80) (AMA) | $C_6$ (II) | 1.4 | 27.0 | −248 |
| Fast Wetting Surfactant 2 (Aerosol ® AY) (AAY) | $C_5$ (III) | 1.8 | 30.1 | −339 |
| Fast Wetting Surfactant 3 (Aerosol ® IB) (AIB) | $C_4$ | 4.0 | 30.1 | −323 |
| Fast Wetting Surfactant Mixture (2:1 Aerosol ® OT/Aerosol ® MA-80) | NA | NA | NA | −295 |

In one example, fibrous structures comprising fibrous elements of the present invention that comprise one or more fast wetting surfactants such that the total level of fast wetting surfactant present in the fibrous structure is from 0.5% to about 1.5% by weight exhibit a wetting rate of less than −185 and/or less than −190 and/or less than −200 and/or less than −245 and/or less than −275 and/or less than −300 and/or less than −320 as measured by the Wetting Rate Test Method described herein.

Fast wetting surfactants according to the present may also be characterized by having structures that are not substantially complexed by the amylose portion of starch. If the amylose complexes the surfactant in the aqueous polymer melt composition, there is less surfactant at the water-air interface of the incipient fibrous elements being formed to lower the surface tension. In addition, the presence of amylose-surfactant complex decreases the dry fibrous structure tensile properties as measured by the Dry Tensile Test Method described herein. The presence of an amylose-surfactant complex can be determined from the Determination of Total Free Surfactant in Fibrous Structure Using Water Extraction/HPLC Test Method described herein. For example, a fibrous structure produced from fibrous elements prepared with 1.3% of a non-fast wetting surfactant; namely, Aerosol® OT (IV) was analyzed by the Determination of Total Free Surfactant in Fibrous Structure Using Water Extraction/HPLC Test Method described herein. The extract contained only 0.49% Aerosol® OT (38% recovery), the rest of the Aerosol® OT surfactant remained with the fibrous structure. In contrast, extract from a fibrous structure produced from fibrous elements prepared with 1.3% of a fast wetting surfactant namely; Aerosol® MA-80 (II), contained 1.1% Aerosol® MA-80 (85% recovery) with only 0.2% Aerosol®MA-80 remaining with the fibrous structure. The fibrous elements of the present invention, which contain one or more fast wetting surfactants of the present invention, produce fibrous structures having greater than 50% fast wetting surfactant recovery after extraction with water according to the Determination of Total Free Surfactant in Fibrous Structure Using Water Extraction/HPLC Test Method described herein. In one example, the fast wetting surfactants of the present invention that do not complex to amylose have chainlengths of less than 8 carbons and the chains have some degree of branching.

In one example, the fast wetting surfactants of the present exhibit surface tensions of less than 39 mN/m$^2$ after 0.1 seconds at a fast wetting surfactant concentration of 1 g/liter at 25° C. as measured with the Dynamic Surface Tension ("Bubble Pressure") Test Method described in Stanislav Dukhin, Gunter Kretzschmar, Reinhard Miller, Dynamics of Adsorption at Liquid Interfaces: Theory, Experiment, Application, p157, incorporated herein by reference. This test method uses a 0.1-2.5% solution of amylose instead of distilled water to probe whether the fast wetting surfactant is complexed by amylose.

A fast wetting surfactant may be present both in the interior and exterior of the fibrous elements produced from the aqueous polymer melt composition, which is distinguished from a surface only treatment of the formed fibrous elements. Any fast wetting surfactant that is present on the exterior of a fibrous element may be determined by extracting the fibrous element with a solvent that dissolves the surfactant, but does not swell the fibrous element and then analyzing for the surfactant by LC-mass spec. The surfactant that is present in the interior of the fibrous element may be determined by extracting the fibrous element with a solvent that dissolves the surfactant and also swells the fibrous elements, such as water/alcohol or water/acetone mixtures followed by analysis for surfactant by a technique such as LC mass spec. Alternatively, the fibrous element may be treated with an enzyme such as amylase that degrades the fibrous element-forming polymer, for example polysaccharide, but not the fast wetting surfactant and the resulting solution may be analyzed for the surfactant by LC-mass spec.

Solid Additives

The fibrous structures and/or sanitary tissue products of the present invention may further comprise one or more solid additives. "Solid additive" as used herein means an additive that is capable of being applied to a surface of a fibrous structure in a solid form. In other words, the solid additive of the present invention can be delivered directly to a surface of a nonwoven substrate without a liquid phase being present, i.e. without melting the solid additive and without suspending the solid additive in a liquid vehicle or carrier. As such, the solid additive of the present invention does not require a liquid state or a liquid vehicle or carrier in order to be delivered to a surface of a nonwoven substrate. The solid additive of the present invention may be delivered via a gas or combinations of gases. In one example, in simplistic terms, a solid additive is an additive that when placed within a container, does not take the shape of the container.

The solid additives of the present invention may have different geometries and/or cross-sectional areas that include round, elliptical, star-shaped, rectangular, trilobal and other various eccentricities.

In one example, the solid additive may exhibit a particle size of less than 6 mm and/or less than 5.5 mm and/or less than 5 mm and/or less than 4.5 mm and/or less than 4 mm and/or less than 2 mm in its maximum dimension.

"Particle" as used herein means an object having an aspect ratio of less than about 25/1 and/or less than about 15/1 and/or less than about 10/1 and/or less than 5/1 to about 1/1. A particle is not a fiber as defined herein.

The solid additives may be present in the fibrous structures of the present invention at a level of greater than about 1 and/or greater than about 2 and/or greater than about 4 and/or to about 20 and/or to about 15 and/or to about 10 g/m$^2$. In one example, a fibrous structure of the present invention comprises from about 2 to about 10 and/or from about 5 to about 10 g/m$^2$ of solid additive.

In one example, the solid additives are present in the fibrous structures of the present invention at a level of greater than 5% and/or greater than 10% and/or greater than 20% to about 50% and/or to about 40% and/or to about 30%.

Non-limiting examples of solid additives of the present invention include fibers, for example pulp fibers. Non-limiting examples of pulp fibers include hardwood pulp fibers, softwood pulp fibers, and mixtures thereof. In one example, the solid additives comprise eucalyptus pulp fibers. In another example, the solid additives include chemically treated pulp fibers.

Scrim Material

The fibrous structure and/or sanitary tissue product may further comprise a scrim material. The scrim material may comprise any suitable material capable of bonding to the nonwoven substrate of the present invention. In one example, the scrim material comprises a material that can be thermally bonded to the nonwoven substrate of the present invention. Non-limiting examples of suitable scrim materials include filaments of the present invention. In one example, the scrim material comprises filaments that comprise hydroxyl polymers. In another example, the scrim material comprises starch filaments. In yet another example, the scrim material comprises filaments comprising a thermoplastic polymer. In still another example, the scrim material comprises a fibrous structure according to the present invention wherein the fibrous structure comprises filaments comprising hydroxyl polymers, such as starch filaments, and/or thermoplastic polymers. In another example, the scrim material may comprise a film. In another example, the scrim material may comprise a nonwoven substrate according to the present invention. In even another example, the scrim material may comprise a latex.

In one example, solid additives are positioned between the scrim material and the nonwoven substrate, for example a surface of the nonwoven substrate. The scrim material may be connected to a surface of the nonwoven substrate, for example at one or more bond sites.

In one example, the scrim material may be the same composition as the nonwoven substrate.

The scrim material may be present in the fibrous structures of the present invention at a basis weight of greater than 0.1 and/or greater than 0.3 and/or greater than 0.5 and/or greater than 1 and/or greater than 2 g/m$^2$ and/or less than 10 and/or less than 7 and/or less than 5 and/or less than 4 g/m$^2$ as determined by the Basis Weight Test Method described herein.

METHODS OF THE PRESENT INVENTION

The methods of the present invention relate to producing polymeric structures, such as fibrous elements, from aqueous polymer melt compositions comprising a fibrous element-forming polymer, such as a hydroxyl polymer, and a fast wetting surfactant.

Methods for Making Fibrous Structure

Figure 2:
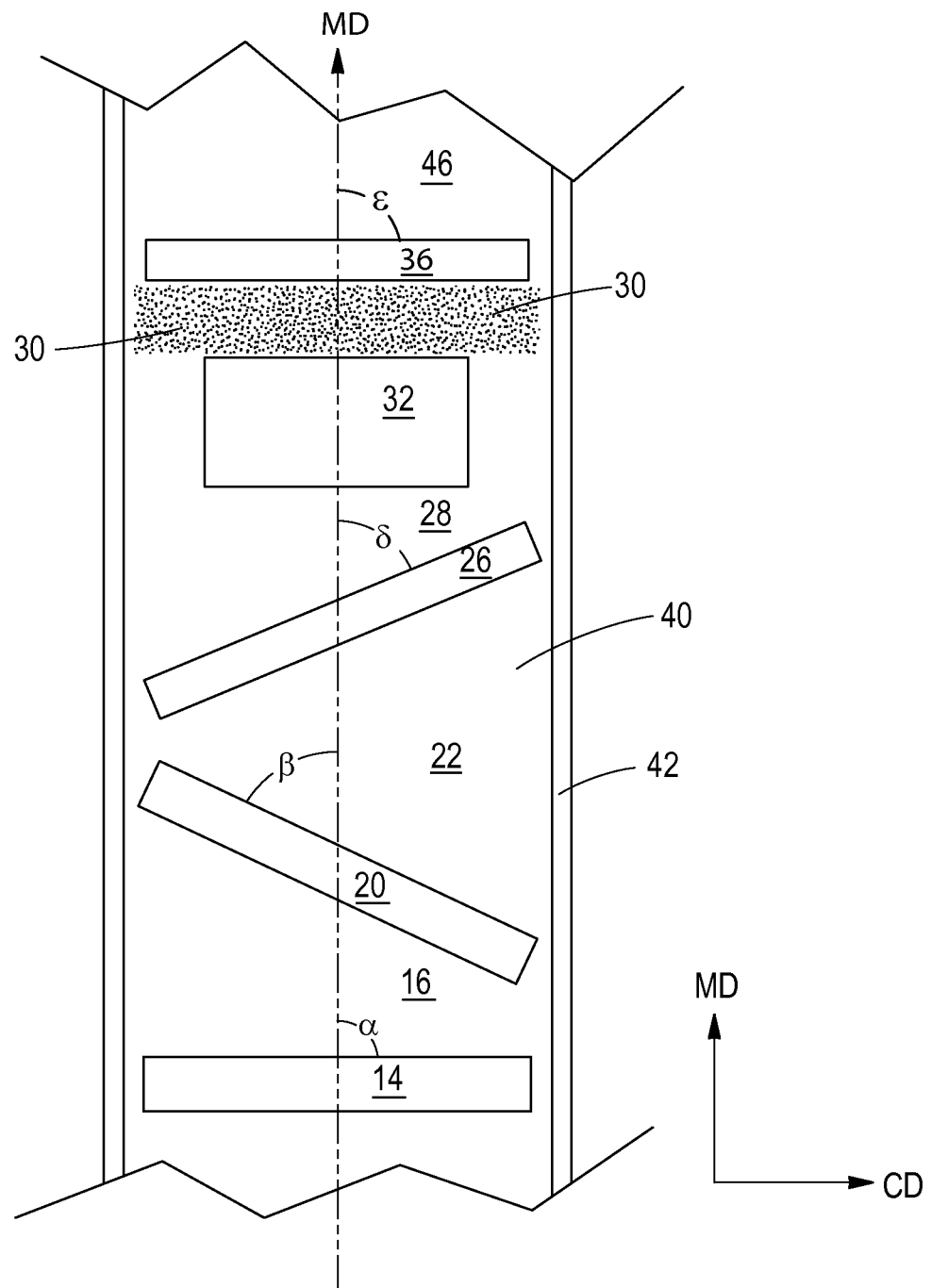
FIG. 2 is a schematic representation of one example of a portion of fibrous structure making process according to the present invention.

FIGS. 1 and 2 illustrate one example of a method for making a fibrous structure of the present invention. As shown in FIGS. 1 and 2, the method 10 comprises the steps of:

a. providing first filaments 12 from a first source 14 of filaments, which form a first layer 16 of filaments;

b. providing second filaments 18 from a second source 20 of filaments, which form a second layer 22 of filaments;

c. providing third filaments 24 from a third source 26 of filaments, which form a third layer 28 of filaments;

d. providing solid additives 30 from a source 32 of solid additives;

e. providing fourth filaments 34 from a fourth source 36 of filaments, which form a fourth layer 38 of filaments; and f. collecting the first, second, third, and fourth filaments 12, 18, 24, 34 and the solid additives 30 to form a fibrous structure 40, wherein the first source 14 of filaments is oriented at a first angle $\alpha$ to the machine direction of the fibrous structure 40, the second source 20 of filaments is oriented at a second angle $\theta$ to the machine direction different from the first angle $\alpha$, the third source 26 is oriented at a third angle $\delta$ to the machine direction different from the first angle $\alpha$ and the second angle $\beta$, and wherein the fourth source 36 is oriented at a fourth angle $\epsilon$ to the machine direction different from the second angle $\beta$ and third angle $\delta$.

The first, second, and third layers 16, 22, 28 of filaments are collected on a collection device 42, which may be a belt or fabric. The collection device 42 may be a patterned belt that imparts a pattern, such as a non-random, repeating pattern to the fibrous structure 40 during the fibrous structure making process. The first, second, and third layers 16, 22, 28 of filaments are collected (for example one on top of the other) on the collection device 42 to form a multi-layer nonwoven substrate 44 upon which the solid additives 30 are deposited. The fourth layer 38 of filaments may then be deposited onto the solid additives 30 to form a scrim 46.

The first angle $\alpha$ and the fourth angle c may be the same angle, for example 90° to the machine direction.

The second angle $\beta$ and the third angle $\delta$ may be the same angle, just positive and negative of one another. For example the second angle $\beta$ may be −40° to the machine direction and the third angle $\delta$ may be +40° to the machine direction.

In one example, at least one of the first, second, and third angles $\alpha$, $\beta$, $\delta$ is less than 90° to the machine direction. In another example, the first angle $\alpha$ and/or fourth angle $\epsilon$ is about 90° to the machine direction. In still another example, the second angle $\beta$ and/or third angle $\delta$ is from about ±10° to about ±80° and/or from about ±30° to about ±60° to the machine direction and/or about ±40° to the machine direction.

In one example, the first, second, and third layers 16, 22, 28 of filaments may be formed into a nonwoven substrate 44 prior to being utilized in the process for making a fibrous structure described above. In this case, the nonwoven substrate 44 would likely be in a parent roll that could be unwound into the fibrous structure making process and the solid additives 30 could be deposited directly onto a surface of the nonwoven substrate 44.

In one example, the step of providing a plurality of solid additives 30 onto the nonwoven substrate 44 may comprise airlaying the solid additives 30 using an airlaying former. A non-limiting example of a suitable airlaying former is available from Dan-Web of Aarhus, Denmark.

In one example, the step of providing fourth filaments 34 such that the filaments contact the solid additives 30 comprises the step of depositing the fourth filaments 34 such that at least a portion (in one example all or substantially all) of the solid additives 30 are contacted by the fourth filaments 34 thus positioning the solid additives 30 between the fourth layer 38 of filaments and the nonwoven substrate 44. Once the fourth layer 38 of filaments is in place, the fibrous structure 40 may be subjected to a bonding step that bonds the fourth layer 38 of filaments (in this case, the scrim 46) to the nonwoven substrate 44. This step of bonding may comprise a thermal bonding operation. The thermal bonding operation may comprise passing the fibrous structure 40 through a nip formed by thermal bonding rolls 48, 50. At least one of the thermal bonding rolls 48, 50 may comprise a pattern that is translated into the bond sites 52 formed in the fibrous structure 40.

In addition to being subjected to a bonding operation, the fibrous structure may also be subjected to other post-processing operations such as embossing, tuft-generating, gear rolling, which includes passing the fibrous structure through a nip formed between two engaged gear rolls, moisture-imparting operations, free-fiber end generating, and surface treating to form a finished fibrous structure. In one example, the fibrous structure is subjected to gear rolling by passing the fibrous structure through a nip formed by at least a pair of gear rolls. In one example, the fibrous structure is subjected to gear rolling such that free-fiber ends are created in the fibrous structure. The gear rolling may occur before or after two or more fibrous structures are combined to form a multi-ply sanitary tissue product. If it occurs after, then the multi-ply sanitary tissue product is passed through the nip formed by at least a pair of gear rolls.

The method for making a fibrous structure of the present invention may be close coupled (where the fibrous structure is convolutedly wound into a roll prior to proceeding to a converting operation) or directly coupled (where the fibrous structure is not convolutedly wound into a roll prior to proceeding to a converting operation) with a converting operation to emboss, print, deform, surface treat, or other post-forming operation known to those in the art. For purposes of the present invention, direct coupling means that the fibrous structure can proceed directly into a converting operation rather than, for example, being convolutedly wound into a roll and then unwound to proceed through a converting operation.

In one example, one or more plies of the fibrous structure according to the present invention may be combined with another ply of fibrous structure, which may also be a fibrous structure according to the present invention, to form a multi-ply sanitary tissue product that exhibits a Tensile Ratio of 2 or less and/or less than 1.7 and/or less than 1.5 and/or less than 1.3 and/or less than 1.1 and/or greater than 0.7 and/or greater than 0.9 as measured according to the Dry Tensile Test Method described herein. In one example, the multi-ply sanitary tissue product may be formed by combining two or more plies of fibrous structure according to the present invention. In another example, two or more plies of fibrous structure according to the present invention may be combined to form a multi-ply sanitary tissue product such that the solid additives present in the fibrous structure plies are adjacent to each of the outer surfaces of the multi-ply sanitary tissue product.

The process of the present invention may include preparing individual rolls of fibrous structure and/or sanitary tissue product comprising such fibrous structure(s) that are suitable for consumer use.

Figure 3:
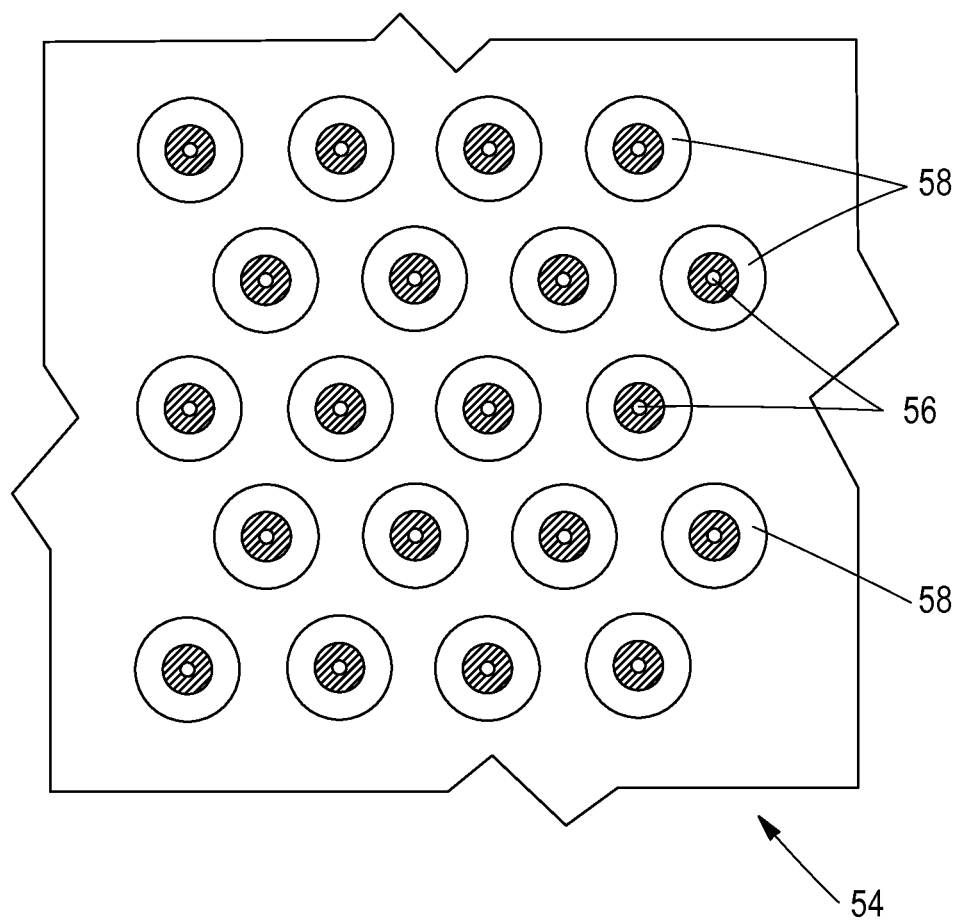
FIG. 3 is a schematic representation of an example of a meltblow die in accordance with the present invention.

In one example, the sources of filaments comprise meltblow dies that produce filaments from a polymer melt composition according to the present invention. In one example, as shown in FIG. 3 the meltblow die 54 may comprise at least one filament-forming hole 56, and/or 2 or more and/or 3 or more rows of filament-forming holes 56 from which filaments are spun. At least one row of the filament-forming holes 56 contains 2 or more and/or 3 or more and/or 10 or more filament-forming holes 56. In addition to the filament-forming holes 56, the meltblow die 54 comprises fluid-releasing holes 58, such as gas-releasing holes, in one example air-releasing holes, that provide attenuation to the filaments formed from the filament-forming holes 56. One or more fluid-releasing holes 58 may be associated with a filament-forming hole 56 such that the fluid exiting the fluid-releasing hole 58 is parallel or substantially parallel (rather than angled like a knife-edge die) to an exterior surface of a filament exiting the filament-forming hole 56. In one example, the fluid exiting the fluid-releasing hole 58 contacts the exterior surface of a filament formed from a filament-forming hole 56 at an angle of less than 30° and/or less than 20° and/or less than 10° and/or less than 5° and/or about 0°. One or more fluid releasing holes 58 may be arranged around a filament-forming hole 56. In one example, one or more fluid-releasing holes 58 are associated with a single filament-forming hole 56 such that the fluid exiting the one or more fluid releasing holes 58 contacts the exterior surface of a single filament formed from the single filament-forming hole 56. In one example, the fluid-releasing hole 58 permits a fluid, such as a gas, for example air, to contact the exterior surface of a filament formed from a filament-forming hole 56 rather than contacting an inner surface of a filament, such as what happens when a hollow filament is formed.

Aqueous Polymer Melt Composition

The aqueous polymer melt composition of the present invention comprises a melt processed fibrous element-forming polymer, such as a melt processed hydroxyl polymer, and a fast wetting surfactant according to the present invention.

The aqueous polymer melt compositions may already be formed or a melt processing step may need to be performed to convert a raw material fibrous element-forming polymer, such as a hydroxyl polymer, into a melt processed fibrous element-forming polymer, such as a melt processed hydroxyl polymer, thus producing the aqueous polymer melt composition. Any suitable melt processing step known in the art may be used to convert the raw material fibrous element-forming polymer into the melt processed fibrous element-forming polymer. "Melt processing" as used herein means any operation and/or process by which a polymer is softened to such a degree that it can be brought into a flowable state.

The aqueous polymer melt compositions of the present invention may have a shear viscosity, as measured according to the Shear Viscosity of a Polymer Melt Composition Measurement Test Method described herein, of from about 0.5 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 $sec^{-1}$ and at the processing temperature (50° C. to 100° C.). The aqueous polymer melt compositions may have a thinning index n value as measured according to the Shear Viscosity of a Polymer Melt Composition Measurement Test Method described herein of from about 0.4 to about 1.0 and/or from about 0.5 to about 0.8.

The aqueous polymer melt compositions may have a temperature of from about 50° C. to about 100° C. and/or from about 65° C. to about 95° C. and/or from about 70° C. to about 90° C. when spinning fibrous elements from the aqueous polymer melt compositions.

In one example, the polymer melt composition of the present invention may comprise from about 30% and/or from about 40% and/or from about 45% and/or from about 50% to about 75% and/or to about 80% and/or to about 85% and/or to about 90% and/or to about 95% and/or to about 99.5% by weight of the aqueous polymer melt composition of a fibrous element-forming polymer, such as a hydroxyl polymer. The fibrous element-forming polymer, such as a hydroxyl polymer, may have a weight average molecular weight greater than 100,000 g/mol as determined by the Weight Average Molecular Weight Test Method described herein prior to any crosslinking.

A fast wetting surfactant is present in the aqueous polymer melt compositions and/or may be added to the aqueous polymer melt composition before polymer processing of the aqueous polymer melt composition.

A non-hydroxyl polymer, such as polyacrylamide, may be present in the aqueous polymer melt composition and/or may be added to the aqueous polymer melt composition before polymer processing of the aqueous polymer melt composition.

A crosslinking system comprising a crosslinking agent, such as an imidazolidinone, and optionally, a crosslinking facilitator, such as an ammonium salt, may be present in the aqueous polymer melt composition and/or may be added to the aqueous polymer melt composition before polymer processing of the aqueous polymer melt composition.

"Crosslinking agent" as used herein means any material that is capable of crosslinking a hydroxyl polymer within a polymer melt composition according to the present. Non-limiting examples of suitable crosslinking agents include polycarboxylic acids and/or imidazolidinones.

"Crosslinking facilitator" as used herein means any material that is capable of activating a crosslinking agent thereby transforming the crosslinking agent from its unactivated state to its activated state. In other words, when a crosslinking agent is in its unactivated state, the hydroxyl polymer present in the polymer melt composition does not undergo unacceptable crosslinking. Unacceptable crosslinking causes the shear viscosity and n value to fall outside the ranges specified which are determined according to the Shear Viscosity of a Polymer Melt Composition Measurement Test Method. In the case of imidazolidinone crosslinkers (such as dihydroxyethyleneurea "DHEU"), the pH and the temperature of the Polymer Melt Composition should be in the desired ranges as measured by the pH of Melt Composition Method and Temperature of Melt Composition Method as described herein; unacceptable crosslinking occur outside these ranges.

When a crosslinking agent in accordance with the present invention is in its activated state, the hydroxyl polymer present in the polymeric structure may and/or does undergo acceptable crosslinking via the crosslinking agent as determined according to the Initial Total Wet Tensile Test Method described herein.

Upon crosslinking the hydroxyl polymer during the curing step, the crosslinking agent becomes an integral part of the polymeric structure as a result of crosslinking the hydroxyl polymer as shown in the following schematic representation:

Hydroxyl polymer-Crosslinking agent-Hydroxyl polymer

The crosslinking facilitator may include derivatives of the material that may exist after the transformation/activation of the crosslinking agent. For example, a crosslinking facilitator salt being chemically changed to its acid form and vice versa.

Nonlimiting examples of suitable crosslinking facilitators include acids having a pKa of less than 6 or salts thereof. The crosslinking facilitators may be Bronsted Acids and/or salts thereof, such as ammonium salts thereof.

In addition, metal salts, such as magnesium and zinc salts, can be used alone or in combination with Bronsted Acids and/or salts thereof, as crosslinking facilitators.

Nonlimiting examples of suitable crosslinking facilitators include benzoic acid, citric acid, formic acid, glycolic acid, lactic acid, maleic acid, phthalic acid, phosphoric acid, hypophosphoric acid, succinic acid, and mixtures thereof and/or their salts, such as their ammonium salts, such as ammonium glycolate, ammonium citrate, ammonium chloride, ammonium sulfate Additional non-limiting examples of suitable crosslinking facilitators include glyoxal bisulfite salts, primary amine salts, such as hydroxyethyl ammonium salts, hydroxypropyl ammonium salt, secondary amine salts, ammonium toluene sulfonate, ammonium benzene sulfonate, ammonium xylene sulfonate, magnesium chloride, and zinc chloride.

Non-Limiting Example—Synthesis of an Aqueous Polymer Melt Composition

An aqueous polymer melt composition of the present invention may be prepared using screw extruders, such as a vented twin screw extruder.

Figure 4A:
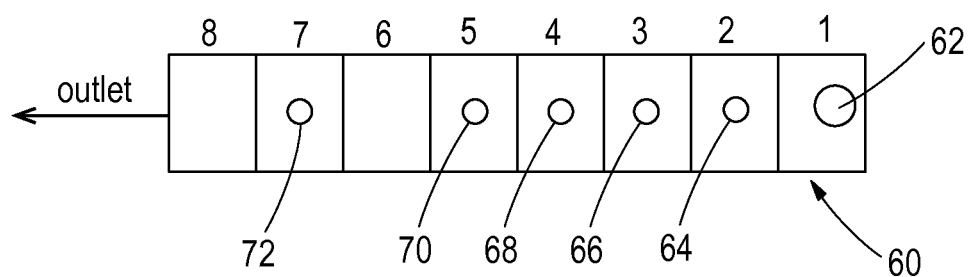
FIG. 4A is a schematic representation of an example of a barrel of a twin screw extruder in accordance with the present invention.

A barrel 60 of an APV Baker (Peterborough, England) 40:1, 58 mm diameter twin screw extruder is schematically illustrated in FIG. 4A. The barrel 60 is separated into eight zones, identified as zones 1-8. The barrel 60 encloses the extrusion screw and mixing elements, schematically shown in FIG. 4B, and serves as a containment vessel during the extrusion process. A solid feed port 62 is disposed in zone 1, a first liquid feed port 64 is disposed in zone 2, a second liquid feed port 66 is disposed in zone 3, a third liquid feed port 68 is disposed in zone 4, and a fourth liquid feed port 70 is disposed in zone 5. A vent 72 is included in zone 7 for cooling and decreasing the liquid, such as water, content of the mixture prior to exiting the extruder. An optional vent stuffer, commercially available from APV Baker, can be employed to prevent the polymer melt composition from exiting through the vent 72. The flow of the aqueous polymer melt composition through the barrel 60 is from zone 1 exiting the barrel 60 at zone 8.

Figure 4B:
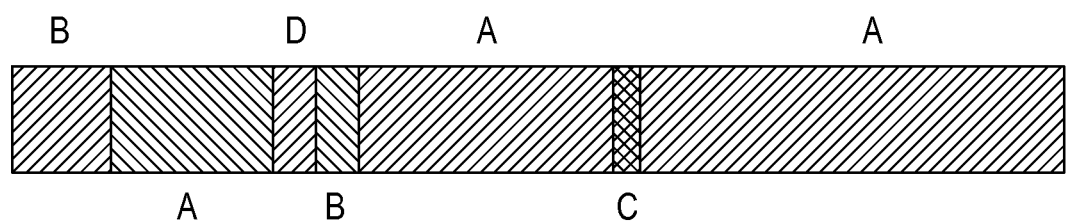
FIG. 4B is a schematic representation of an example of a screw and mixing element configuration for the twin screw extruder of FIG. 4A.

A screw and mixing element configuration for the twin screw extruder is schematically illustrated in FIG. 4B. The twin screw extruder comprises a plurality of twin lead screws (TLS) (designated A and B) and paddles (designated C) and reverse twin lead screws (RTLS) (designated D) installed in series as illustrated in Table 1 below.

TABLE 1

| Zone | Total Length Ratio | Element | Pitch | Length Ratio | Element Type |
|---|---|---|---|---|---|
| 1 | 1.5 | TLS | 1 | 1.5 | A |
| 1 | 3.0 | TLS | 1 | 1.5 | A |
| 1 | 4.5 | TLS | 1 | 1.5 | A |
| 2 | 6.0 | TLS | 1 | 1.5 | A |
| 2 | 7.5 | TLS | 1 | 1.5 | A |
| 2 | 9.0 | TLS | 1 | 1.5 | A |
| 3 | 10.5 | TLS | 1 | 1.5 | A |
| 3 | 12.0 | TLS | 1 | 1.5 | A |
| 3 | 13.0 | TLS | 1 | 1 | A |
| 3 | 14.0 | TLS | 1 | 1 | A |
| 4 | 15.0 | TLS | 1 | 1 | A |
| 4 | 16.0 | TLS | 1 | 1 | A |
| 4 | 16.3 | PADDLE | 0 | 0.25 | C |
| 4 | 16.5 | PADDLE | 0 | 0.25 | C |
| 4 | 18.0 | TLS | 1 | 1.5 | A |
| 4 | 19.5 | TLS | 1 | 1.5 | A |
| 5 | 21.0 | TLS | 1 | 1.5 | A |
| 5 | 22.5 | TLS | 1 | 1.5 | A |
| 5 | 24.0 | TLS | 1 | 1.5 | A |
| 5 | 25.0 | TLS | 1 | 1 | A |
| 6 | 25.3 | TLS | 1 | 0.25 | A |
| 6 | 26.3 | TLS | 1 | 1 | A |
| 6 | 27.3 | TLS | 1 | 1 | A |
| 6 | 28.3 | TLS | 0.5 | 1 | B |
| 6 | 29.3 | TLS | 0.5 | 1 | B |
| 6 | 29.8 | RTLS | 0.5 | 0.5 | D |
| 7 | 30.3 | RTLS | 0.5 | 0.5 | D |
| 7 | 30.8 | RTLS | 0.5 | 0.5 | D |
| 7 | 32.3 | TLS | 1 | 1.5 | A |
| 7 | 33.8 | TLS | 1 | 1.5 | A |
| 7 | 34.8 | TLS | 1 | 1 | A |
| 8 | 35.8 | TLS | 1 | 1 | A |
| 8 | 36.8 | TLS | 0.5 | 1 | B |
| 8 | 37.8 | TLS | 0.5 | 1 | B |
| 8 | 38.8 | TLS | 0.5 | 1 | B |
| 8 | 40.3 | TLS | 0.5 | 1.5 | B |

Screw elements (A-B) are characterized by the number of continuous leads and the pitch of these leads. A lead is a flight (at a given helix angle) that wraps the core of the screw element. The number of leads indicates the number of flights wrapping the core at any given location along the length of the screw. Increasing the number of leads reduces the volumetric capacity of the screw and increases the pressure generating capability of the screw.

The pitch of the screw is the distance needed for a flight to complete one revolution of the core. It is expressed as the number of screw element diameters per one complete revolution of a flight. Decreasing the pitch of the screw increases the pressure generated by the screw and decreases the volumetric capacity of the screw.

The length of a screw element is reported as the ratio of length of the element divided by the diameter of the element.

This example uses TLS and RTLS. Screw element type A is a TLS with a 1.0 pitch and varying length ratios. Screw element type B is a TLS with a 0.5 pitch and varying length ratios.

Bilobal paddles, C, serving as mixing elements, are also included in series with the SLS and TLS screw elements in order to enhance mixing. Paddle C has a length ratio of ¼. Various configurations of bilobal paddles and reversing elements D, single and twin lead screws threaded in the opposite direction, are used in order to control flow and corresponding mixing time. Screw element D is a RTLS with a 0.5 pitch and a 0.5 length ratio.

In zone 1, one or more fibrous element-forming polymers, such as one or more hydroxyl polymers, are fed into the solid feed port 62 at a rate of 330 grams/minute using a K-Tron (Pitman, N.J.) loss-in-weight feeder. These hydroxyl polymers are combined inside the extruder (zone 2) with a fast wetting surfactant (Aerosol® MA-80) added at liquid feed port 64 (zone 2) at a rate of 12 grams/minute. Water, an external plasticizer, is added at the liquid feed port 66 (zone 3) at a rate of 160 grams/minute using a Milton Roy (Ivyland, Pa.) diaphragm pump (1.9 gallon per hour pump head) to form a hydroxyl polymer/fast wetting surfactant/water slurry. A crosslinking facilitator, such as ammonium chloride, may be added to the slurry at liquid feed port 66 (zone 3) also. Another fibrous element-forming polymer, such as a hydroxyl polymer, for example polyvinyl alcohol, may be added to the slurry at liquid feed port 68 (zone 4). A non-hydroxyl polymer, such as polyacrylamide may be added to the slurry at liquid feed port 70 (zone 5). Additional additives such as other surfactants, other non-hydroxyl polymers, other salts and/or acids may be added at various feed ports along the length of the barrel 60. This slurry is then conveyed down the barrel 60 of the extruder and cooked to produce an aqueous polymer melt composition comprising a melt processed hydroxyl polymer and a fast wetting surfactant. Table 2 describes the temperature, pressure, and corresponding function of each zone of the extruder.

TABLE 2

| Zone | Temp. (° F.) | Pressure | Description of Screw | Purpose |
|---|---|---|---|---|
| 1 | 70 | Low | Feeding/Conveying | Feeding and Mixing |
| 2 | 70 | Low | Conveying | Mixing and Conveying |
| 3 | 70 | Low | Conveying | Mixing and Conveying |
| 4 | 130 | Low | Pressure/Decreased Conveying | Conveying and Heating |
| 5 | 355 | Medium | Pressure Generating | Cooking at Pressure and Temperature |
| 6 | 355 | High | Reversing | Cooking at Pressure and Temperature |
| 7 | 355 | Low | Conveying | Cooling and Conveying (with venting) |
| 8 | 355 | Low | Pressure Generating | Conveying |

Figure 5A:
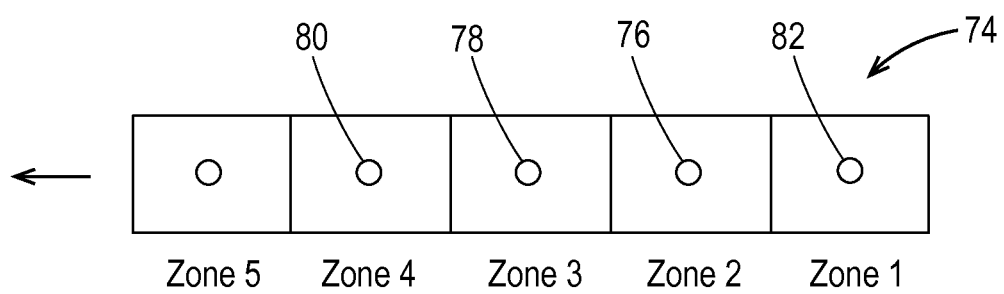
FIG. 5A is a schematic representation of an example of a barrel of a twin screw extruder suitable for use in the present invention.
Figure 5B:
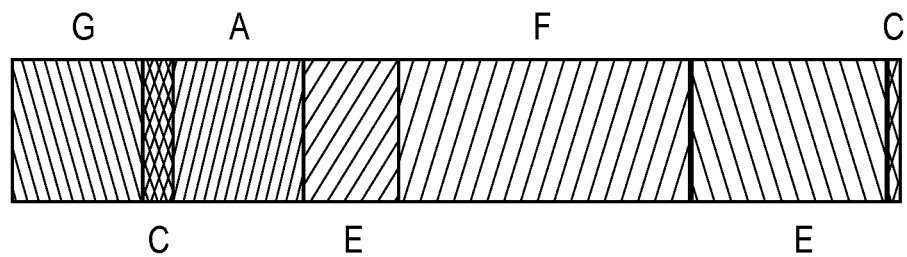
FIG. 5B is a schematic representation of an example of a screw and mixing element configuration suitable for use in the barrel of FIG. 5A.

After the aqueous polymer melt composition exits the first extruder, part of the aqueous polymer melt composition is dumped and another part (450 g) is fed into a Mahr (Charlotte, N.C.) gear pump and pumped to a second extruder. The second extruder provides a means to cool the polymer melt composition by venting the polymer melt composition to atmospheric pressure and provides additional points to incorporate additives. A barrel 74 of an APV Baker (Peterborough, England) 13:1, 70 mm diameter twin screw extruder is schematically illustrated in FIG. 5A as the second extruder. The barrel 74 is separated into five zones, identified as zones 1-5. The barrel 74 encloses the extrusion screw and mixing elements, schematically shown in FIG. 5B, and serves as containment vessel during the extrusion process. A first liquid feed port 76 is disposed in zone 2, a second liquid feed port 78 is disposed in zone 3, and a third liquid feed port 80 is disposed in zone 4. A vent 82 is included in zone 1 for cooling and decreasing the liquid, such as water, content of the mixture prior to exiting the second extruder. An optional vent stater, commercially available from APV Baker, can be employed to prevent the aqueous polymer melt composition from exiting through the vent 82. The flow of the aqueous polymer melt composition through the barrel 74 is from zone 2 exiting the barrel 74 at zone 5.

A screw and mixing element configuration for the second extruder consists of twin lead screws (TLS) (designated A, E, F), paddles (designated C), and single lead screws (SLS) (designated G) installed in series as illustrated in Table 3 below.

TABLE 3

| Zone | Total Length Ratio | Element | Pitch | Length Ratio | Element Type | Purpose |
|---|---|---|---|---|---|---|
| 1 | 0.25 | Paddle | 0 | 0.25 | C | Mixing |
| 1 | 1.75 | TLS | 2 | 1.5 | E | Vent Location |
| 2 | 3.25 | TLS | 2 | 1.5 | E | Conveying |
| 2 | 4.75 | TLS | 3 | 1.5 | F | Feed Inlet Location |
| 3 | 6.25 | TLS | 3 | 1.5 | F | Conveying |
| 3 | 7.75 | TLS | 3 | 1.5 | F | Conveying |
| 4 | 9.25 | TLS | 2 | 1.5 | E | Conveying |
| 4 | 10.25 | TLS | 1 | 1 | A | Conveying |
| 4 | 11.25 | TLS | 1 | 1 | A | Conveying |
| 4 | 11.38 | Paddle | 0 | 0.125 | C | Mixing |
| 4 | 11.50 | Paddle | 0 | 0.125 | C | Mixing |
| 5 | 11.63 | Paddle | 0 | 0.125 | C | Mixing |
| 5 | 11.75 | Paddle | 0 | 0.125 | C | Mixing |
| 5 | 12.75 | SLS | 0.5 | 1 | G | Conveying |
| 5 | 13.75 | SLS | 0.5 | 1 | G | Conveying |

The aqueous polymer melt composition comprising the melt processed hydroxyl polymer and fast wetting surfactant coming from the first extruder is fed into the second extruder at a point about 5 L/D down the barrel, liquid feed port 76 (zone 2). A vent 82 open to atmospheric pressure is situated at about 1.5 L/D down the barrel 74 (zone 1). Some water vapor escapes from the aqueous polymer melt composition and exits through the vent 82. Water, an external plasticizer, and a crosslinking facilitator, such as ammonium chloride, may be added at the liquid feed port 78 (zone 3). A non-hydroxyl polymer, such as polyacrylamide, may be added at liquid feed port 80 (zone 4). Additional additives such as other surfactants, other non-hydroxyl polymers, other salts and/or acids may be added at various feed ports along the length of the barrel 74. The aqueous polymer melt composition is then conveyed through the extruder to the end of the barrel 74 (zone 5).

At least a portion of the aqueous polymer melt composition is then dumped and another part (400 g) is fed into a Mahr (Charlotte, N.C.) gear pump and pumped into a SMX style static mixer (Koch-Glitsch, Woodridge, Ill.). The static mixer is used to combine additional additives such as crosslinking agents, for example an imidazolidinone, crosslinking facilitators, such as ammonium chloride, external plasticizers, such as water, with the aqueous polymer melt composition comprising the melt processed hydroxyl polymer and fast wetting surfactant. The additives are pumped into the static mixer via PREP 100 HPLC pumps (Chrom Tech, Apple Valley Minn.). These pumps provide high pressure, low volume addition capability. The aqueous polymer melt composition of the present invention is now ready to be processed by a polymer processing operation.

b. Polymer Processing

"Polymer processing" as used herein means any operation and/or process by which a polymeric structure comprising a processed hydroxyl polymer is formed from an aqueous polymer melt composition comprising a melt processed hydroxyl polymer. Non-limiting examples of polymer processing operations include extrusion, molding and/or fiber spinning. Extrusion and molding (either casting or blown), typically produce films, sheets and various profile extrusions. Molding may include injection molding, blown molding and/or compression molding. Fiber spinning may include spun bonding, melt blowing, rotary spinning, continuous filament producing and/or tow fiber producing.

A "processed hydroxyl polymer" as used herein means any hydroxyl polymer that has undergone a melt processing operation and a subsequent polymer processing operation.

c. Polymeric Structure

The aqueous polymer melt composition can be subjected to one or more polymer processing operations such that the polymer melt composition is processed into a polymeric structure comprising the hydroxyl polymer and a crosslinking system according to the present invention.

"Polymeric structure" as used herein means any physical structure formed as a result of processing an aqueous polymer melt composition in accordance with the present invention. Non-limiting examples of polymeric structures in accordance with the present invention include fibrous elements (such as filaments and/or fibers), films and/or foams.

A crosslinking system via a crosslinking agent and optionally a crosslinking facilitator may crosslink the processed hydroxyl polymers together to produce the polymeric structure of the present invention, with or without being subjected to a curing step. In other words, the crosslinking system in accordance with the present invention acceptably crosslinks the processed hydroxyl polymers of a processed polymer melt composition together via the crosslinking agent to form an integral polymeric structure, such as a fibrous element. The crosslinking agent can function as a "building block" for the polymeric structure. In one example, without the crosslinking agent, no polymeric structure in accordance with the present invention could be formed.

Polymeric structures of the present invention do not include coatings and/or other surface treatments that are applied to a pre-existing form, such as a coating on a fibrous element, film or foam. However, in one example of the present invention, a polymeric structure, such as a fibrous element, in accordance with the present invention may be coated and/or surface treated with a crosslinking system of the present invention.

In one example, the polymeric structure produced via a polymer processing operation may be cured at a curing temperature of from about 110° C. to about 215° C. and/or from about 110° C. to about 200° C. and/or from about 120° C. to about 195° C. and/or from about 130° C. to about 185° C. for a time period of from about 0.01 and/or 1 and/or 5 and/or 15 seconds to about 60 minutes and/or from about 20 seconds to about 45 minutes and/or from about 30 seconds to about 30 minutes. Alternative curing methods may include radiation methods such as UV, e-beam, IR and other temperature-raising methods.

Further, the polymeric structure may also be cured at room temperature for days, either after curing at above room temperature or instead of curing at above room temperature.

The polymeric structure may exhibit an initial total wet tensile, as measured by the Initial Total Wet Tensile Test Method described herein, of at least about 1.18 g/cm (3 g/in) and/or at least about 1.57 g/cm (4 g/in) and/or at least about 1.97 g/cm (5 g/in) to about 23.62 g/cm (60 g/in) and/or to about 21.65 g/cm (55 g/in) and/or to about 19.69 g/cm (50 g/in).

The polymeric structures of the present invention may include melt spun fibers and/or spunbond fibers, staple fibers, hollow fibers, shaped fibers, such as multi-lobal fibers and multicomponent fibers, especially bicomponent fibers. The multicomponent fibers, especially bicomponent fibers, may be in a side-by-side, sheath-core, segmented pie, ribbon, islands-in-the-sea configuration, or any combination thereof. The sheath may be continuous or non-continuous around the core. The ratio of the weight of the sheath to the core can be from about 5:95 to about 95:5. The fibers of the present invention may have different geometries that include round, elliptical, star shaped, rectangular, and other various eccentricities.

One or more polymeric structures of the present invention may be incorporated into a multi-polymeric structure product, such as a fibrous structure and/or web, if the polymeric structures are in the form of fibers. Such a multi-polymeric structure product may ultimately be incorporated into a commercial product, such as a single- or multi-ply sanitary tissue product, such as facial tissue, bath tissue, paper towels and/or wipes, feminine care products, diapers, writing papers, cores, such as tissue cores, and other types of paper products.

Non-limiting examples of processes for preparing polymeric structures in accordance with the present invention follow.

i) Fibrous Element Formation

Figure 6:
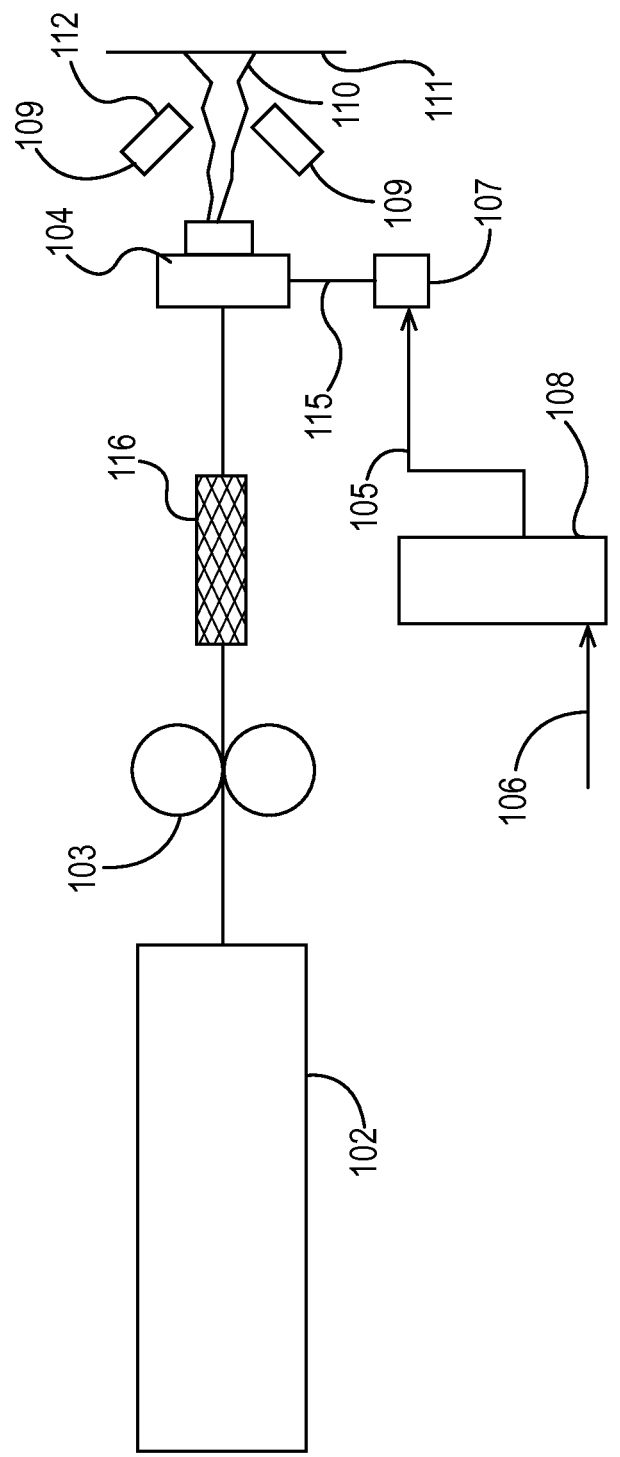
FIG. 6 is a schematic representation of an example of a process for synthesizing a fibrous element in accordance with the present invention.

An aqueous polymer melt composition comprising a melt processed hydroxyl polymer and a fast wetting surfactant is prepared according to the Synthesis of an Aqueous Polymer Melt Composition described above. As shown in FIG. 6, the aqueous polymer melt composition may be processed into a fibrous element. The aqueous polymer melt composition present in an extruder 102 is pumped to a die 104 using pump 103, such as a Zenith®, type PEP II, having a capacity of 10 cubic centimeters per revolution (cc/rev), manufactured by Parker Hannifin Corporation, Zenith Pumps division, of Sanford, N.C., USA. The aqueous polymer melt composition's flow to die 104 is controlled by adjusting the number of revolutions per minute (rpm) of the pump 103. Pipes connecting the extruder 102, the pump 103, the die 104, and optionally a mixer 116 are electrically heated and thermostatically controlled to 65° C.

Figure 7:
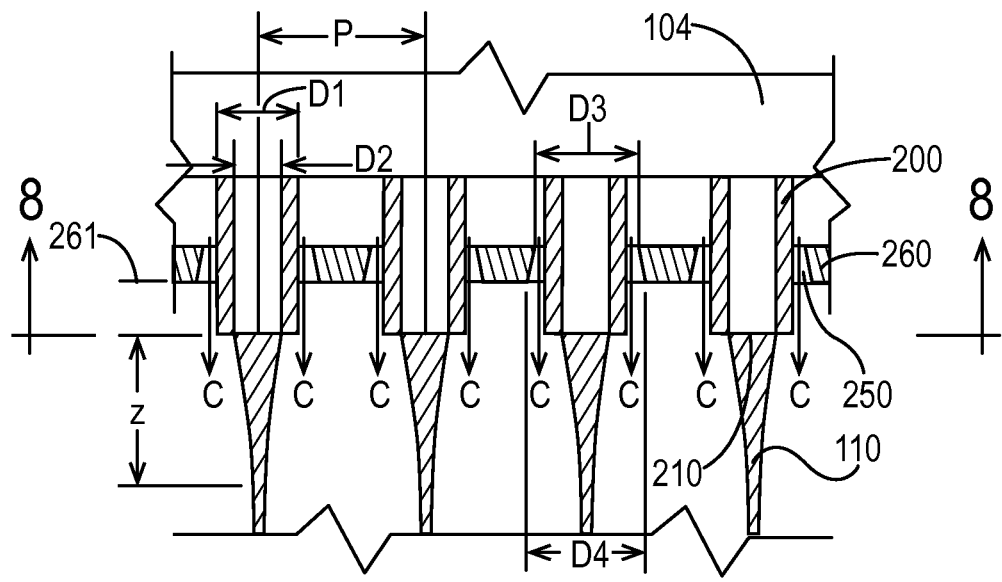
FIG. 7 is a schematic representation of a partial side view of the process shown in FIG. 6 showing an example of an attenuation zone.
Figure 8:
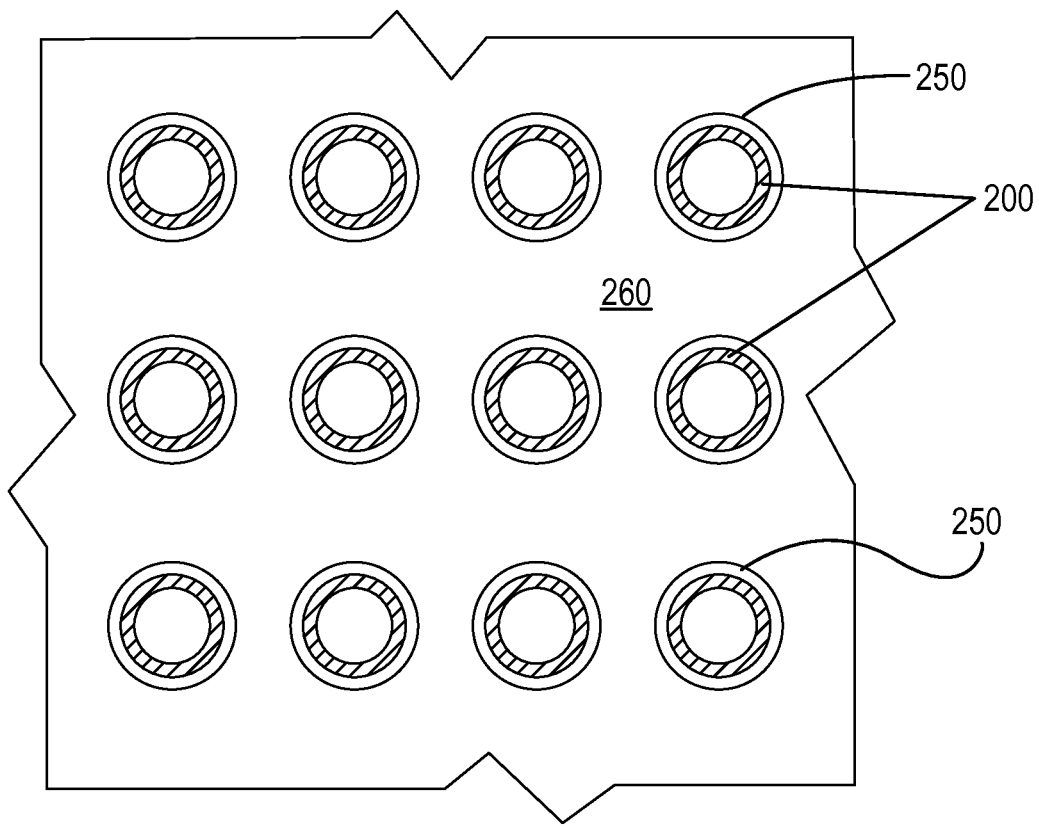
FIG. 8 is a schematic plan view taken along lines 8-8 of FIG. 7 and showing one possible arrangement of a plurality of extrusion nozzles arranged to provide fibrous elements of the present invention.
Figure 9:
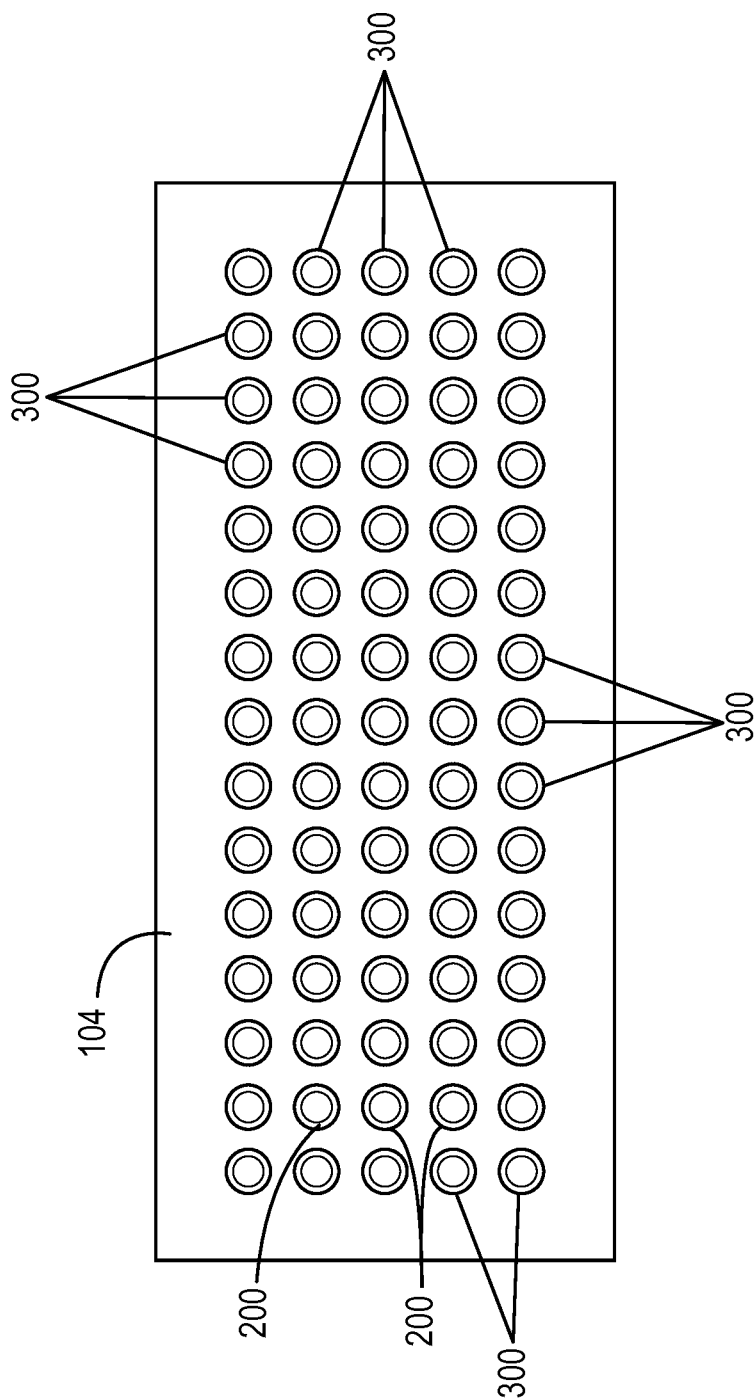
FIG. 9 is a view similar to that of FIG. 8 and showing one possible arrangement of orifices for providing a boundary air around the attenuation zone shown in FIG. 7.
Figure 10:
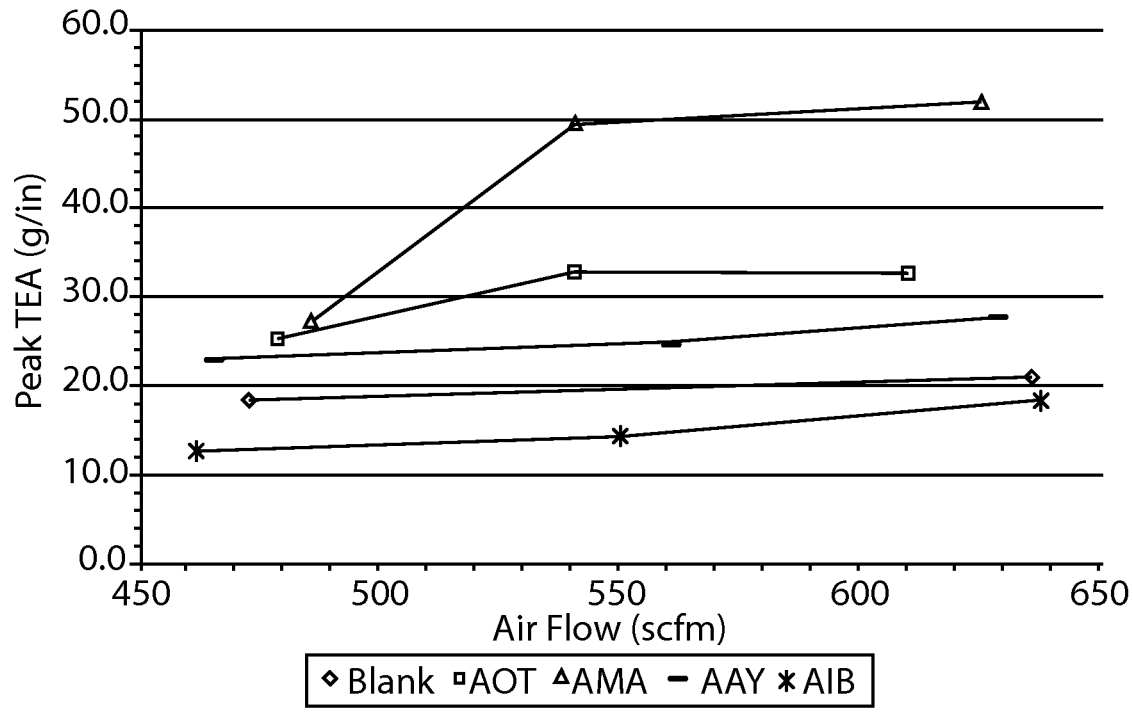
FIG. 10 is a plot of Air Flow (scfm) to Peak TEA (g/in) for fibrous structures.
Figure 11:
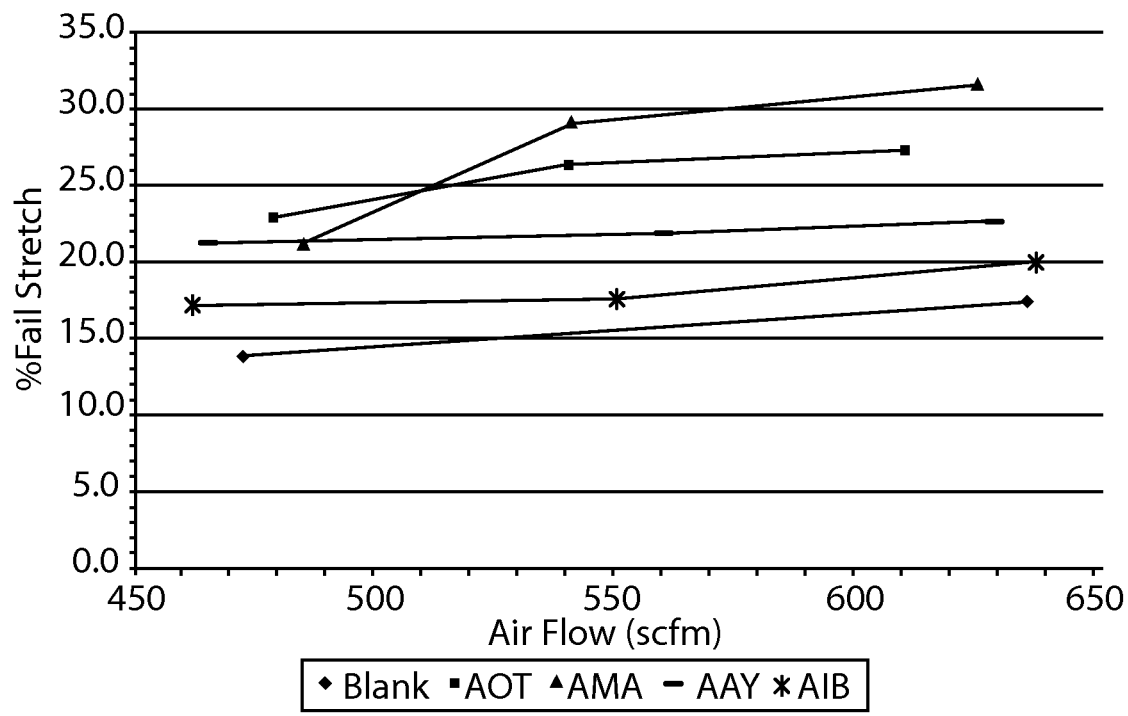
FIG. 11 is a plot of Air Flow (scfm) to % Fail Stretch for fibrous structures.

The die 104 has several rows of circular extrusion nozzles 200 spaced from one another at a pitch P (FIG. 7) of about 2.489 millimeters (about 0.098 inches). The nozzles are arranged in a staggered grid with a spacing of 2.489 millimeters (about 0.098 inches) within rows and a spacing of 2.159 millimeters (about 0.085 inches) between rows. The nozzles 200 have individual inner diameters D2 of about 0.254 millimeters (about 0.010 inches) and individual outside diameters (D1) of about 0.813 millimeters (about 0.032 inches). Each individual nozzle 200 is encircled by an annular orifice 250 formed in a plate 260 (FIGS. 7 and 8) having a thickness of about 1.9 millimeters (about 0.075 inches). A pattern of a plurality of the orifices 250 in the plate 260 correspond to a pattern of extrusion nozzles 200. Once the orifice plate is combined with the dies, the resulting area for airflow is about 36 percent. The plate 260 is fixed so that the embryonic filaments 110 being extruded through the nozzles 200 are surrounded and attenuated by generally cylindrical, humidified air streams supplied through the orifices 250. The nozzles can extend to a distance from about 1.5 mm to about 4 mm, and more specifically from about 2 mm to about 3 mm, beyond a surface 261 of the plate 260 (FIG. 7). As shown in FIG. 9, a plurality of boundary-air orifices 300, is formed by plugging nozzles of two outside rows on each side of the plurality of nozzles, as viewed in plane, so that each of the boundary-layer orifice comprised a annular aperture 250 described herein above. Additionally, every other row and every other column of the remaining capillary nozzles are blocked, increasing the spacing between active capillary nozzles.

As shown in FIG. 6, attenuation air can be provided by heating compressed air from a source 106 by an electrical-resistance heater 108, for example, a heater manufactured by Chromalox, Division of Emerson Electric, of Pittsburgh, Pa., USA. An appropriate quantity of steam 105 at an absolute pressure of from about 240 to about 420 kiloPascals (kPa), controlled by a globe valve (not shown), is added to saturate or nearly saturate the heated air at the conditions in the electrically heated, thermostatically controlled delivery pipe 115. Condensate is removed in an electrically heated, thermostatically controlled, separator 107. The attenuating air has an absolute pressure from about 130 kPa to about 310 kPa, measured in the pipe 115. The filaments 110 being extruded have a moisture content of from about 20% and/or from about 25% to about 50% and/or to about 55% by weight. The filaments 110 are dried by a drying air stream 109 having a temperature from about 149° C. (about 300° F.) to about 315° C. (about 600° F.) by an electrical resistance heater (not shown) supplied through drying nozzles 112 and discharged at an angle generally perpendicular relative to the general orientation of the embryonic fibers being extruded. The filaments 110 are dried from about 45% moisture content to about 15% moisture content (i.e., from a consistency of about 55% to a consistency of about 85%) and are collected on a collection device 111, such as, for example, a movable foraminous belt.

The process parameters are as follows in Table 4.

TABLE 4

| Sample | Units | |
| --- | --- | --- |
| Attenuation Air Flow Rate | G/min | 9000 |
| Attenuation Air Temperature | ° C. | 65 |
| Attenuation Steam Flow Rate | G/min | 1800 |
| Attenuation Steam Gage Pressure | kPa | 213 |
| Attenuation Gage Pressure in Delivery Pipe | kPa | 14 |
| Attenuation Exit Temperature | ° C. | 65 |
| Solution Pump Speed | Revs/min | 12 |
| Solution Flow | G/min/hole | 0.18 |
| Drying Air Flow Rate | g/min | 17000 |
| Air Duct Type | | Slots |
| Air Duct Dimensions | mm | 356 × 127 |
| Velocity via Pitot-Static Tube | M/s | 65 |
| Drying Air Temperature at Heater | ° C. | 260 |
| Dry Duct Position from Die | mm | 80 |
| Drying Duct Angle Relative to Fibers | degrees | 0 |
| Drying Duct to Drying Duct Spacing | mm | 205 |
| Die to Forming Box distance | Mm | 610 |
| Forming Box Machine direction Length | Mm | 635 |
| Forming Box Cross Direction Width | Mm | 380 |
| Forming Box Flowrate | g/min | 41000 | ii) Foam Formation

The aqueous polymer melt composition for foam formation may be prepared similarly as for fibrous element formation except that the added water content may be less, typically from about 10-21% of the hydroxyl polymer weight. With less water to plasticize the hydroxyl polymer, higher temperatures are needed in extruder zones 5-8 (FIG. 4A), typically from about 150-250° C. Also with less water available, it may be necessary to add the crosslinking system, especially the crosslinking agent, with the water in zone 1. In order to avoid premature crosslinking in the extruder, the aqueous polymer melt composition pH should be between 7 and 8, achievable by using a crosslinking facilitator e.g., ammonium salt. A die is placed at the location where the extruded material emerges and is typically held at about 160-210° C. Modified high amylose starches (for example greater than 50% and/or greater than 75% and/or greater than 90% by weight of the starch of amylose) granulated to particle sizes ranging from about 400-1500 microns may be used in the present invention. It may also be advantageous to add a nucleating agent such as microtalc or alkali metal or alkaline earth metal salt such as sodium sulfate or sodium chloride in an amount of about 1-8% of the starch weight. The foam may be shaped into various forms.

iii) Film Formation

The aqueous polymer melt composition for film formation may be prepared similarly as for foam formation except that the added water content may be less, typically 3-15% of the hydroxyl polymer weight and a polyol external plasticizer such as glycerol is included at about 10-30% of the hydroxyl polymer weight. As with foam formation, zones 5-7 (FIG. 4A) are held at about 160-210° C., however, the slit die temperature is lower between 60-120° C. As with foam formation, the crosslinking system, especially the crosslinking agent, may be added along with the water in zone 1 and the aqueous polymer melt composition pH may be between about 7-8 achievable by using a crosslinking facilitator e.g., ammonium salt.

Non-Limiting Example of Fibrous Structure of Present Invention

With reference to FIG. 4A, an aqueous polymer melt composition comprising 25% CPI 058020 acid thinned dent corn starch (hydroxyl polymer) from Corn Products International and 25% Ethylex 2035 acid thinned hydroxyethyl starch (hydroxyl polymer) from Tate and Lyle and 6.5% Mowiol 10-98 98% hydrolyzed polyvinylalcohol (hydroxyl polymer) from Kururay, 0.22% Hyperfloc NF221 polyacrylamide (non-hydroxyl polymer), 0.56% Aerosol® MA-80 (fast wetting surfactant) and 43% water (external plasticizer), is prepared according to Synthesis of Aqueous Polymer Melt Composition of the present invention. Both starches are added to the extruder at solid feed port 62, polyvinylalcohol is added as a 43% aqueous solution at liquid feed port 68, polyacrylamide is added as a 2.2% aqueous solution at liquid feed port 70, and fast wetting surfactant is added as a 70% aqueous propylene glycol/water solution at liquid feed port 64. To this aqueous polymer melt composition is added a crosslinking agent (DHEU) (20% aqueous solution), a crosslinking facilitator (ammonium chloride) (25% aqueous solution), and water at a static mixer to produce an aqueous polymer melt composition comprising about 18.5% CPI 058020 acid thinned dent corn starch, 18.5% Ethylex 2035 acid thinned hydroxyethyl starch, 4.83% Mowiol 10-98 98% hydrolyzed polyvinylalcohol, 0.165% Hyperfloc NF221 polyacrylamide, 1.1% ammonium chloride, 3.93% DHEU, 0.66% sulfosuccinate surfactant, and 50% water.

Fibrous elements are formed from the polymer melt composition in accordance with Synthesis of Polymeric Structure of the present invention. Fibrous elements are formed at three different drying air flows (21620 g/min, 18630 g/min, and 16309 g/min) for each surfactant and are collected on a moving foraminous belt. A vacuum is used to remove air while leaving the fibers to form as a fibrous structure on the belt. The belt transports the fibrous structure to subsequent equipment, all of which operate at about 0.20 meters/second (40 feet/minute). The fibrous structure feeds through a thermal bonding nip consisting of two heated metal rolls. The rolls are 0.133 meters in diameter and are heated to about 165° C. (330° F.). One roll is smooth, the other has square knobs representing 12.8% of the surface area; the knobs are 0.508 mm wide on a 1.499 mm grid. The rolls are loaded with about 18900 Newtons per linear meter of roll (about 108 pounds per linear inch). The fibrous structure continues to a heating oven cure the fibrous structure. The fibrous structure is supported on a separate foraminous belt and feeds through a 1.054 meter long oven operating at 171° C. (340° F.) circulating about 13600 grams per minute of heated air. The fibrous structure continues to another foraminous belt where the fibrous structure is humidified to about 7 percent moisture by the addition of steam. Steam is supplied by an Armstrong International series 9000 conditioned-steam humidifier. Finally the fibrous structure is wound onto a paper core.

The cured fibrous structure are characterized by basis weight, initial total wet tensile, dry peak TEA and dry fail stretch and fiber diameter according to the Test Methods described herein. The resulting data is shown in Table 5 for the examples set forth therein. Prior to testing, samples are conditioned overnight at a relative humidity of 48% to 50% and within a temperature range of 22° C. to 24° C.

TABLE 5

| Example | Surfactant | Drying Air Flow (g/min) | Normalized Dry Peak TEA (g/in) | Dry Fail Stretch (%) | Normalized ITWT (g/in) |
|---|---|---|---|---|---|
| 1 | None | 22254.3 | 20.7 | 17.6 | 84.5 |
| 2 | None | 16573.9 | 18.4 | 13.9 | 86.0 |
| 3 | AOT | 21354.9 | 32.4 | 27.3 | 97.5 |
| 4 | AOT | 18921.6 | 32.3 | 26.5 | 104.8 |
| 5 | AOT | 16784.2 | 25.4 | 22.8 | 115.5 |
| 6 | AMA | 21876.6 | 51.8 | 31.7 | 109.1 |
| 7 | AMA | 18939.1 | 49.8 | 29.4 | 111.2 |
| 8 | AMA | 17017.8 | 27.4 | 21.3 | 106.2 |
| 9 | AIB | 22320.5 | 18.4 | 19.8 | 52.2 |
| 10 | AIB | 19272.0 | 14.8 | 17.7 | 50.5 |
| 11 | AIB | 16188.5 | 12.8 | 17.2 | 51.8 |
| 12 | AAY | 22005.1 | 27.8 | 22.8 | 55.8 |
| 13 | AAY | 19622.4 | 24.6 | 22.0 | 49.1 |
| 14 | AAY | 16311.1 | 22.8 | 21.3 | 53.7 |

Test Methods of the Present Invention

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 12 hours prior to the test. All plastic and paper board packaging articles of manufacture, if any, must be carefully removed from the samples prior to testing. The samples tested are "usable units." "Usable units" as used herein means sheets, flats from roll stock, pre-converted flats, and/or single or multi-ply products. Except where noted all tests are conducted in such conditioned room, all tests are conducted under the same environmental conditions and in such conditioned room. Discard any damaged product. Do not test samples that have defects such as wrinkles, tears, holes, and like. All instruments are calibrated according to manufacturer's specifications.

Shear Viscosity of a Polymer Melt Composition Measurement Test Method

The shear viscosity of a polymer melt composition comprising a crosslinking system is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the polymer melt composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta = K\gamma^{n-1}$, wherein K is the material's viscosity constant, n is the material's thinning index and $\gamma$ is the shear rate. The reported apparent shear viscosity of the composition herein is calculated from an interpolation to a shear rate of 3,000 sec$^{-1}$ using the power law relation.

Basis Weight Test Method

Basis weight of a fibrous structure is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 square in stack)×(No. of squares in stack)]

For example,

Basis Weight (lbs/3000 ft$^2$)=[[Mass of stack (g)/ 453.6 (g/lbs)]/[12.25 (in$^2$)/144 (in$^2$/ft$^2$)×12]]× 3000 or,

Basis Weight (g/m$^2$)=Mass of stack (g)/[79.032 (cm$^2$)/10,000 (cm$^2$/m$^2$)×12]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Initial Total Wet Tensile Test Method

Cut tensile strips precisely in the direction indicated; four to the machine direction (MD) and four to the cross direction (CD). Cut the sample strips 4 in. (101.6 mm) long and exactly 1 in. (25.4 mm) wide using an Alpha Precision Sample Cutter Model 240-7A (pneumatic): Thwing-Albert Instrument Co and an appropriate die.

An electronic tensile tester (Thwing-Albert EJA Vantage Tester, Thwing-Albert Instrument Co., 10960 Dutton Rd., Philadelphia, Pa., 19154) is used and operated at a crosshead speed of 4.0 inch (about 10.16 cm) per minute, using a strip of a fibrous structure of 1 inch wide and a length of about 4 inches long. The gauge length is set to 1 inch. The strip is inserted into the jaws with the 1 inch wide section in the clamps, verifying that the sample is hanging straight into the bottom jaw. The sample is then pre-loaded with 20-50 g/in of pre-load force. This tension is applied to the web to define the adjusted gauge length, and, by definition is the zero strain point. The sample is then wet thoroughly with water using a syringe to gently apply the water on the uppermost portion of the web sample inside the jaws. Crosshead movement is then initiated within 3-8 seconds after initial water contact. The initial result of the test is an array of data in the form load (grams force) versus crosshead displacement (centimeters from starting point).

The sample is tested in two orientations, referred to here as MD (machine direction, i.e., in the same direction as the continuously wound reel and forming fabric) and CD (cross-machine direction, i.e., 90° from MD). The MD and CD wet tensile strengths are determined using the above equipment and calculations in the following manner:

Initial Total Wet Tensile=ITWT $(g_f/\text{inch})$=Peak Load$_{MD}$ $(g_f)/2$ (inch$_{width}$)+Peak Load$_{CD}$ $(g_f)/2$ (inch$_{width}$)

The Initial Total Wet Tensile value is then normalized for the basis weight of the strip from which it was tested. The normalized basis weight used is 24 g/m², and is calculated as follows:

Normalized {ITWT}={ITWT}*24 (g/m²)/Basis Weight of Strip (g/m²)

In one example, the initial total wet tensile of a polymeric structure, such as a fibrous structure, of the present invention is at least 1.18 g/cm (3 g/in) and/or at least 1.57 g/cm (4 g/in) and/or at least 1.97 g/cm (5 g/in) then the crosslinking system is acceptable. The initial total wet tensile may be less than or equal to about 23.62 g/cm (60 g/in) and/or less than or equal to about 21.65 g/cm (55 g/in) and/or less than or equal to about 19.69 g/cm (50 g/in).

Dry Tensile Strength Test Method

Elongation (Stretch), Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the load cell. Both the movable (upper) and stationary (lower) pneumatic jaws are fitted with smooth stainless steel faced grips, with a design suitable for testing 1 inch wide sheet material (Thwing-Albert item #733GC). An air pressure of about 60 psi is supplied to the jaws.

Eight usable units of fibrous structures are divided into two stacks of four usable units each. The usable units in each stack are consistently oriented with respect to machine direction (MD) and cross direction (CD). One of the stacks is designated for testing in the MD and the other for CD. Using a one inch precision cutter (Thwing-Albert JDC-1-10, or similar) take a CD stack and cut one, 1.00 in ±0.01 in wide by 3-4 in long stack of strips (long dimension in CD). In like fashion cut the remaining stack in the MD (strip's long dimension in MD), to give a total of 8 specimens, four CD and four MD strips. Each strip to be tested is one usable unit thick, and will be treated as a unitary specimen for testing.

Program the tensile tester to perform an extension test, collecting force and extension data at an acquisition rate of 20 Hz as the crosshead raises at a rate of 2.00 in/min (5.08 cm/min) until the specimen breaks. The break sensitivity is set to 80%, i.e., the test is terminated when the measured force drops to 20% of the maximum peak force, after which the crosshead is returned to its original position.

Set the gage length to 1.00 inch. Zero the crosshead and load cell. Insert the specimen into the upper and lower open grips such that at least 0.5 inches of specimen length is contained in each grip. Align specimen vertically within the upper and lower jaws, then close the upper grip. Verify specimen is aligned, then close lower grip. The specimen should be fairly straight between grips, with no more than 5.0 g of force on the load cell. Add a pre-tension force of 3 g. This tension is applied to the specimen to define the adjusted gauge length, and, by definition is the zero strain point. Start the tensile tester and data collection. Repeat testing in like fashion for all four CD and four MD specimens. Program the software to calculate the following from the constructed force (g) verses extension (in) curve.

Eight samples are run on the Tensile Tester (four to the MD and four to the CD) and average of the respective dry total tensile, dry peak TEA and dry Fail Stretch is reported as the Dry Total Tensile, Dry peak TEA and Dry Fail Stretch. Peak TEA is defined as tensile energy absorbed (area under the load vs. strain tensile curve) from zero strain to peak force point, with units of g/in. Dry Fail Stretch is defined as the percentage strain measured after the web is strained past its peak load point, where the force drops to exactly 50% of its peak load force.

The dry peak TEA is then normalized for the basis weight of the strip from which it was tested. The normalized basis weight used is 24 g/m², and is calculated as follows:

Normalized {dry peak TEA}={dry peak TEA}*24 (g/m²)/Basis Weight of Strip (g/m²)

The MD and CD dry tensile strengths are determined using the above equipment and calculations in the following manner.

Tensile Strength in general is the maximum peak force (g) divided by the specimen width (1 in), and reported as g/in to the nearest 1 g/in.

Average Tensile Strength=sum of tensile loads measures (MD)/(Number of tensile stripes tested (MD)*Number of useable units or plys per tensile stripe)

This calculation is repeated for cross direction testing.

Dry Total Tensile=Average MD tensile strength+ Average CD tensile strength

The Dry Tensile value is then normalized for the basis weight of the strip from which it was tested. The normalized basis weight used is 24 g/m², and is calculated as follows:

Normalized {DTT}={DTT}*24 (g/m²)/Basis Weight of Strip (g/m²)

The various values are calculated for the four CD specimens and the four MD specimens. Calculate an average for each parameter separately for the CD and MD specimens.

Water Content of a Polymer Melt Composition Test Method

A water content of a polymer melt composition is determined as follows. A weighed sample of a polymer melt composition (4-10 g) is placed in a 120° C. convection oven for 8 hours. The sample is reweighed after removing from the oven. The % weight loss is recorded as the water content of the melt.

Polymer Melt Composition pH Test Method

A polymer melt composition pH is determined by adding 25 mL of the polymer melt composition to 100 mL of deionized water, stirring with a spatula for 1 min and measuring the pH.

Weight Average Molecular Weight Test Method

The weight average molecular weight (Mw) of a material, such as a hydroxyl polymer is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, Mass., USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, Calif., USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, N.H., USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, Calif., USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Relative Humidity Test Method

Relative humidity is measured using wet and dry bulb temperature measurements and an associated psychometric chart. Wet bulb temperature measurements are made by placing a cotton sock around the bulb of a thermometer. Then the thermometer, covered with the cotton sock, is placed in hot water until the water temperature is higher than an anticipated wet bulb temperature, more specifically, higher than about 82° C. (about 180° F.). The thermometer is placed in the attenuating air stream, at about 3 millimeters (about ⅛ inch) from the extrusion nozzle tips. The temperature will initially drop as the water evaporates from the sock. The temperature will plateau at the wet bulb temperature and then will begin to climb once the sock loses its remaining water. The plateau temperature is the wet bulb temperature. If the temperature does not decrease, then the water is heated to a higher temperature. The dry bulb temperature is measured using a 1.6 mm diameter J-type thermocouple placed at about 3 mm downstream from the extrusion nozzle tip.

Based on a standard atmospheric psychometric chart or an Excel plug-in, such as for example, "MoistAirTab" manufactured by ChemicaLogic Corporation, a relative humidity is determined Relative Humidity can be read off the chart, based on the wet and dry bulb temperatures.

Air Velocity Test Method

A standard Pitot tube is used to measure the air velocity. The Pitot tube is aimed into the air stream, producing a dynamic pressure reading from an associated pressure gauge. The dynamic pressure reading, plus a dry bulb temperature reading is used with the standard formulas to generate an air velocity. A 1.24 mm (0.049 inches) Pitot tube, manufactured by United Sensor Company of Amherst, N.H., USA, is connected to a hand-held digital differential pressure gauge (manometer) for the velocity measurements.

Average Diameter Test Method

A fibrous structure comprising fibrous elements of appropriate basis weight (approximately 5 to 20 grams/square meter) is cut into a rectangular shape, approximately 20 mm by 35 mm. The sample is then coated using a SEM sputter coater (EMS Inc, PA, USA) with gold so as to make the fibers relatively opaque. Typical coating thickness is between 50 and 250 nm. The sample is then mounted between two standard microscope slides and compressed together using small binder clips. The sample is imaged using a 10× objective on an Olympus BHS microscope with the microscope light-collimating lens moved as far from the objective lens as possible. Images are captured using a Nikon D1 digital camera. A Glass microscope micrometer is used to calibrate the spatial distances of the images. The approximate resolution of the images is 1 μm/pixel. Images will typically show a distinct bimodal distribution in the intensity histogram corresponding to the fibers and the background. Camera adjustments or different basis weights are used to achieve an acceptable bimodal distribution. Typically 10 images per sample are taken and the image analysis results averaged.

The images are analyzed in a similar manner to that described by B. Pourdeyhimi, R. and R. Dent in "Measuring fiber diameter distribution in nonwovens" (Textile Res. J. 69(4) 233-236, 1999). Digital images are analyzed by computer using the MATLAB (Version. 6.1) and the MATLAB Image Processing Tool Box (Version 3.) The image is first converted into a grayscale. The image is then binarized into black and white pixels using a threshold value that minimizes the intraclass variance of the thresholded black and white pixels. Once the image has been binarized, the image is skeltonized to locate the center of each fiber in the image. The distance transform of the binarized image is also computed. The scalar product of the skeltonized image and the distance map provides an image whose pixel intensity is either zero or the radius of the fiber at that location. Pixels within one radius of the junction between two overlapping fibers are not counted if the distance they represent is smaller than the radius of the junction. The remaining pixels are then used to compute a length-weighted histogram of fiber diameters contained in the image.

Degradation of Fibrous Structure Test Method

Approximately 2 g of a fibrous structure comprised of a fibrous element-forming polymer, such as starch, and a non-hydroxyl polymer, such as a polyacrylamide, is placed into a 30 mL pressure tube with 14 g of 1N HCl, and heated to 130° C. for 45 minutes. The solution is filtered through a glass microfiber with 1 m pore size, and neutralized to pH 7 with sodium bicarbonate. Assuming no loss of the non-hydroxyl polymer, the solution is run through a gel permeation chromatography column using the Weight Average Molecular Weight Method with the following changes:

Samples are injected, without dilution, after being filtered with a Whatman GD/X nylon, 5 μm syringe filter. The column used is a Waters Linear Ultrahydrogel (molecular weight ranges from 100 to 7,000,000 g/mol) measuring 7.8×300 mm. The column temperature is 50° C. and the injection volume is 100 μl. The aqueous mobile phase contains 0.03M potassium phosphate, 0.2M sodium nitrate and 0.02% sodium azide. The mobile phase is adjusted to pH7 with sodium hydroxide. Run time is 25 minutes.

Determination of Total Free Surfactant in Fibrous Structure Using Water Extraction/HPLC Test Method The amount of total free surfactant in a fibrous structure is determined by placing a 0.5 g sample of the fibrous structure in 10 mL of distilled water in a glass vial with lid for 18 hours. After the 18 hours, shake vigorously for 1 minute. Next remove a 2-3 mL aliquot of the liquid ("extract") from the glass vial with a syringe. Place a syringe filter (GHP Acrodisc 25 mm syringe filter with 0.45 μm GHP membrane) on the syringe and deliver the extract in the syringe to a scintillation vial. Determine the weight of the extract in the scintillation vial. Add an amount of acetonitrile to the extract to make a 70:30 acetonitrile:extract mixture. Remove a 1-2 mL aliquot of the acetonitrile:extract mixture with a syringe. Place a syringe filter (GHP Acrodisc 25 mm syringe filter with 0.45 μm GHP membrane) on the syringe and deliver the acetonitrile:extract in the syringe to an HPLC vial. HPLC is run to characterize the extract. Linear regression is used to calculate the total amount of free surfactant extracted from the fibrous structure.

HPLC Conditions:

Mobile phase: 0.005M tetrabutylammonium phosphate in 70:30 acetonitrile:water.
Column: Waters Bondapak C18 3.9×150 mm
Flow Rate: 0.5 mL
UV detector @ 214 nm
Extraction: 0.5 gm web in 10 mL water or acetone Wetting Rate Test Method 1. The syringe and tubing of the DAT Fibro 1100 system are rinsed with Millipore Water 3 times.
2. The syringe is loaded with Millipore 18 MΩ water and the air bubbles are eliminated from the top before inserting into the instrument.
3. The DAT Fibro 1100 is calibrated with the calibration standard provided by the manufacturer. After calibration the height, base, volume, and angle should be within target. If not, make the necessary adjustments following the manufacturer's instructions.

| Calibration Targets | |
|---|---|
| Height | 0.93 ± 0.02 mm |
| Base | 1.99 ± 0.05 mm |
| Volume | 1.87 ± 0.05 μL |
| Angle | 85.9° ± 1° |

4. From each fibrous structure, strips are cut to obtain 8 measurements for each sample block. The fibrous structures are handled with clean tweezers. Minimum contact with the measured surface of the fibrous structure is required.
5. The fibrous structures are placed onto the sample block with double sided tape. The fibrous structures must lay flat on the sample block with no bending or curling in order to obtain an accurate measurement.
6. The following conditions are used for the Contact Angle Tester:

| | | |
|---|---|---|
| Liquid: Millipore Water | Steps: 1 | References Lines |
| Timeout 0.3 min | Minimum height: 7 | Mod threshold: 0 |
| # Of Drops 8 | Minimum width: 10 | Cannula Tip: 442 |
| Drop size 10 microliter | Capture Offset: 0 | Drop bottom: 305 |
| Stroke pulse 15 | Travel time: 10 | Paper Position: 77 |
| Time collected: 0.01 sec | Pump delay: 2 | Batch Mode: Manual |
| 0.02 sec | | |
| 0.03 sec | | |

7. When measuring the contact angle it is important that the drop be applied to the sample surface with as little force and bouncing as possible. Therefore it may be necessary to adjust the sample height and tubing in order to assure that the drop is applied properly and the measurement recorded accurately.
8. Once all the data has been collected it is saved as a *.DAT file which is then opened in the analysis program JMP.
9. In JMP the time and angle measurements are plotted, resulting in an exponential decay curve. This curve fits the first order rate equation $A=A_0e^{-kt}$ where k is the wetting rate of the fibrous structure.
10. The measurements time and angle values are combined and plotted.
11. The rate equation is then fitted to the points to determine $A_0$ and k for the sample set. The standard deviation is also calculated in JMP. The standard deviation for each value is defined as the product of the square root of the mean squared error and the square root of the diagonals of the derivative cross-products matrix inverse.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toilet tissue comprising a monocomponent fibrous element produced from an aqueous polymer melt composition void of thermoplastic water-insoluble polymers and comprising a blend comprising a monocomponent non-thermoplastic fibrous element-forming polymer, water, and a branched fast wetting surfactant selected from the group consisting of: sulfosuccinate surfactants, alcohol sulfate surfactants derived from branched alcohols, paraffin sulfonates, and mixtures thereof wherein the branched fast wetting surfactant facilitates removal of water from the monocomponent fibrous element during formation from the aqueous polymer melt composition, wherein the fibrous element exhibits greater than 50% fast wetting surfactant recovery after extraction with water according to the Determination of Total Free Surfactant in Fibrous Structure Using Water Extraction/HPLC Test Method.

2. The toilet tissue according to claim 1 wherein the fibrous element-forming polymer comprises a hydroxyl polymer.

3. The toilet tissue according to claim 2 wherein the hydroxyl polymer comprises a polysaccharide.

4. The toilet tissue according to claim 1 wherein the fibrous element-forming polymer is selected from the group consisting of: polyvinyl alcohol, polyvinyl alcohol derivatives, polyvinyl alcohol copolymers, gums, arabinans, galactans, proteins, and mixtures thereof.

5. The toilet tissue according to claim 1 wherein the blend comprises two or more fibrous element-forming polymers.

6. The toilet tissue according to claim 1 wherein the fast wetting surfactant is selected from the group consisting of: anionic surfactants, cationic surfactants, nonionic surfactants, zwitterionic surfactants, and mixtures thereof.

7. The toilet tissue according to claim 1 wherein the fast wetting surfactant comprises a sulfosuccinate surfactant.

8. The toilet tissue according to claim 1 wherein the blend further comprises a non-hydroxyl polymer selected from the group consisting of: polyacrylamide and its derivatives; polyacrylic acid, polymethacrylic acid, and their esters; polyethyleneimine; copolymers made from mixtures of monomers of the aforementioned polymers; and mixtures thereof.

9. The toilet tissue according to claim 8 wherein the non-hydroxyl polymer comprises polyacrylamide.

10. The toilet tissue according to claim 1 wherein the fibrous element comprises a filament.

11. The toilet tissue according to claim 1 wherein the toilet tissue comprises a plurality of fibrous elements according to claim 1.

12. The toilet tissue according to claim 11 wherein the toilet tissue further comprises one or more solid additives.

13. The toilet tissue according to claim 12 wherein at least one of the one or more solid additives comprises a fiber.

14. The toilet tissue according to claim 12 wherein the toilet tissue further comprises a scrim connected to the surface of the toilet tissue such that the solid additives are positioned between the scrim and the surface of the toilet tissue.

15. The toilet tissue according to claim 1 wherein the toilet tissue exhibits a basis weight of from about 10 $g/m^2$ to about 120 $g/m^2$.

16. The toilet tissue according to claim 1 wherein the fibrous element is a crosslinked fibrous element.

* * * * *